(12) United States Patent
Chalvignac

(10) Patent No.: US 9,308,345 B2
(45) Date of Patent: Apr. 12, 2016

(54) BREATHING ASSISTANCE DEVICE COMPRISING A GAS REGULATING VALVE AND ASSOCIATED BREATHING ASSISTANCE METHOD

(71) Applicant: ResMed Paris SAS, Paris (FR)

(72) Inventor: Philippe Auguste Chalvignac, Moissy Cramayel (FR)

(73) Assignee: ResMed Paris SAS (FR)

( * ) Notice: Subject to any disclaimer, the term of this patent is extended or adjusted under 35 U.S.C. 154(b) by 190 days.

(21) Appl. No.: 14/017,709

(22) Filed: Sep. 4, 2013

(65) Prior Publication Data

US 2014/0007876 A1 Jan. 9, 2014

Related U.S. Application Data

(63) Continuation of application No. 11/919,463, filed as application No. PCT/EP2006/061989 on May 2, 2006, now Pat. No. 8,544,464.

(30) Foreign Application Priority Data

May 2, 2005 (WO) .................. PCT/IB2005/001454

(51) Int. Cl.
*A61M 16/20* (2006.01)
*A61M 16/00* (2006.01)

(52) U.S. Cl.
CPC ........... *A61M 16/20* (2013.01); *A61M 16/0057* (2013.01); *A61M 16/204* (2014.02); *A61M 16/205* (2014.02); *A61M 16/206* (2014.02); *A61M 16/209* (2014.02); *A61M 16/0066* (2013.01); *A61M 2016/0027* (2013.01); *A61M 2016/0036* (2013.01);
(Continued)

(58) Field of Classification Search
CPC . A61M 16/20; A61M 16/201; A61M 16/202; A61M 16/203; A61M 16/204; A61M 16/205; A61M 16/206; A61M 16/207
See application file for complete search history.

(56) References Cited

U.S. PATENT DOCUMENTS 1,990,130 A 2/1935 Moos
3,429,552 A 2/1969 Huley et al.
(Continued)

FOREIGN PATENT DOCUMENTS

EP 0615764 A1 9/1994
EP 0990448 A2 4/2000
(Continued)

OTHER PUBLICATIONS

Translation of Offiicial Action JPA 2008-509440.
(Continued)

*Primary Examiner* — Lynne Anderson
(74) *Attorney, Agent, or Firm* — Lerner, David, Littenberg, Krumholz & Mentlik, LLP

(57) ABSTRACT

The invention relates to a breathing assistance device for a patient, the device including: a source of respiratory pressurised gas; a gas transmission duct comprising a distal end coupled to said source and a proximal end coupled to the patient; a gas regulating valve interposed in the gas transmission duct at a proximal location, comprising a leakage orifice and an obstruction means capable of varying the opening of the leakage orifice upon signal of controlling means and allowing a bidirectional gas flow through the leakage orifice in both expiration and inspiration phases.

36 Claims, 38 Drawing Sheets

(52) U.S. Cl.
CPC ............. *A61M 2016/0042* (2013.01); *A61M 2202/0208* (2013.01); *A61M 2205/8206* (2013.01)

(56) References Cited

U.S. PATENT DOCUMENTS

| | | | |
|---|---|---|---|
| 3,831,596 A | 8/1974 | Cavallo | |
| 4,318,399 A | 3/1982 | Berndtsson | |
| 4,336,590 A | 6/1982 | Jacq et al. | |
| 4,344,144 A | 8/1982 | Damico et al. | |
| 4,494,537 A | 1/1985 | Gottlieb | |
| 4,611,591 A | 9/1986 | Inui et al. | |
| 4,798,689 A | 1/1989 | Heim et al. | |
| 4,903,693 A | 2/1990 | Yasue | |
| 4,928,684 A | 5/1990 | Breitenfelder et al. | |
| 4,971,108 A | 11/1990 | Gottlieb | |
| 5,273,031 A | 12/1993 | Olsson et al. | |
| 5,305,739 A | 4/1994 | Gray | |
| 5,339,807 A | 8/1994 | Carter | |
| 5,398,673 A | 3/1995 | Lambert | |
| 5,398,676 A | 3/1995 | Press et al. | |
| 5,400,777 A | 3/1995 | Olsson et al. | |
| 5,484,270 A | 1/1996 | Adahan | |
| 5,598,838 A | 2/1997 | Servidio et al. | |
| 5,787,882 A | 8/1998 | Hamilton | |
| 6,024,088 A | 2/2000 | Ishikawa et al. | |
| 6,029,660 A | 2/2000 | Calluaud et al. | |
| 6,371,110 B1 | 4/2002 | Peterson et al. | |
| 6,443,154 B1 | 9/2002 | Jalde et al. | |
| 6,990,977 B1 | 1/2006 | Calluaud et al. | |
| 7,201,166 B2 | 4/2007 | Blaise et al. | |
| 7,273,052 B2 | 9/2007 | Gossweiler | |
| 7,552,731 B2 | 6/2009 | Jorczak et al. | |
| 7,658,786 B2 | 2/2010 | Lin | |
| 7,681,573 B2 | 3/2010 | Matthiessen et al. | |
| 7,753,049 B2 | 7/2010 | Jorczak et al. | |
| 7,779,834 B2 | 8/2010 | Calluaud et al. | |
| D631,542 S | 1/2011 | DeGross et al. | |
| 2002/0170562 A1 | 11/2002 | Lurie et al. | |
| 2003/0066530 A1 | 4/2003 | Shahbazpour et al. | |
| 2004/0007232 A1 | 1/2004 | Rochat | |
| 2004/0069305 A1 | 4/2004 | Niemela et al. | |
| 2004/0194783 A1 | 10/2004 | McAuliffe et al. | |
| 2008/0092891 A1 | 4/2008 | Cewers | |
| 2010/0282251 A1 | 11/2010 | Calluaud et al. | |

FOREIGN PATENT DOCUMENTS

| | | |
|---|---|---|
| EP | 1059096 A3 | 10/2001 |
| EP | 1197238 A2 | 4/2002 |
| WO | 98/26830 A1 | 6/1998 |
| WO | 02/23678 A1 | 3/2002 |

OTHER PUBLICATIONS

Translation of Official Office Action JPA 2008-509440.

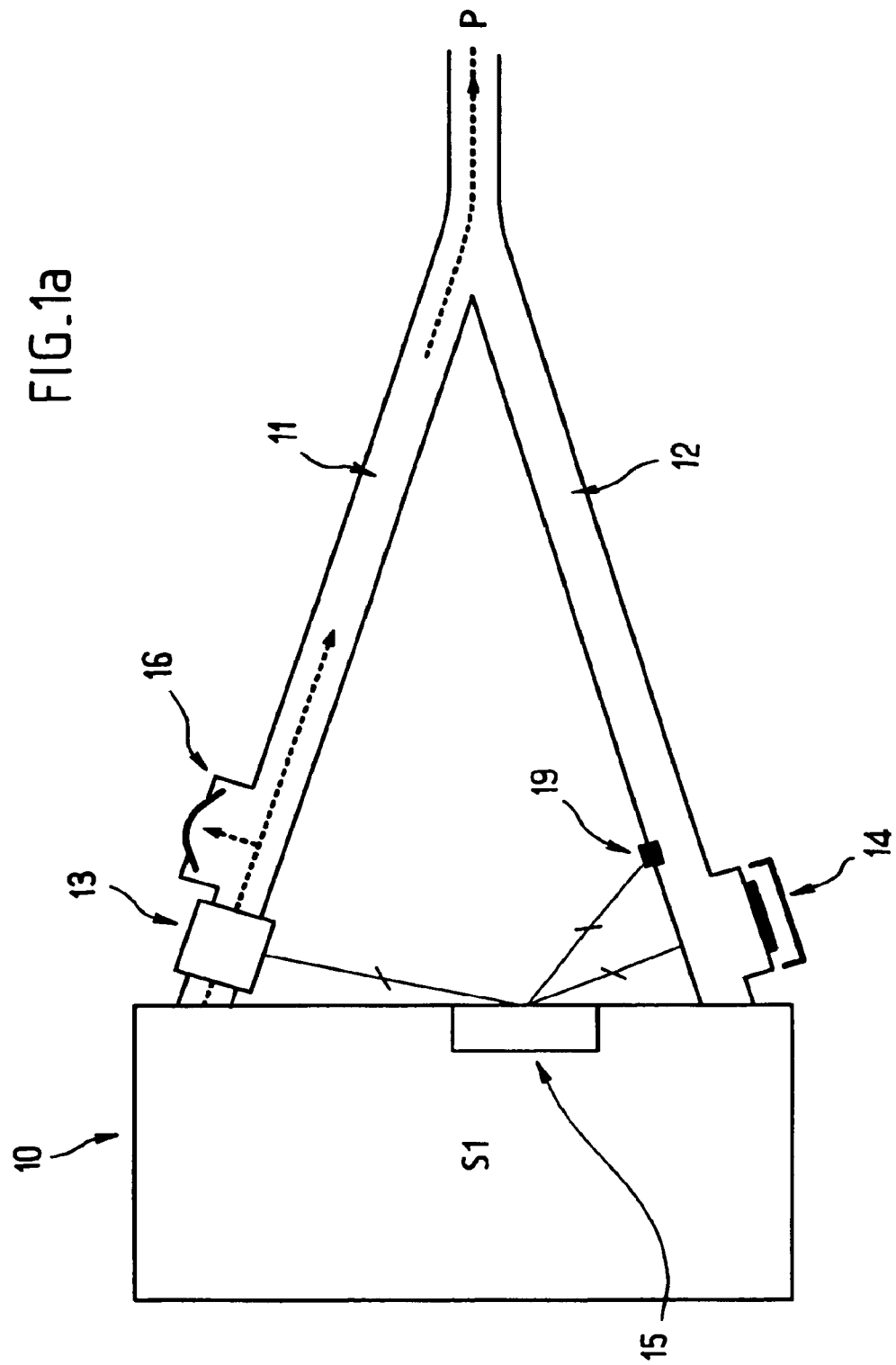

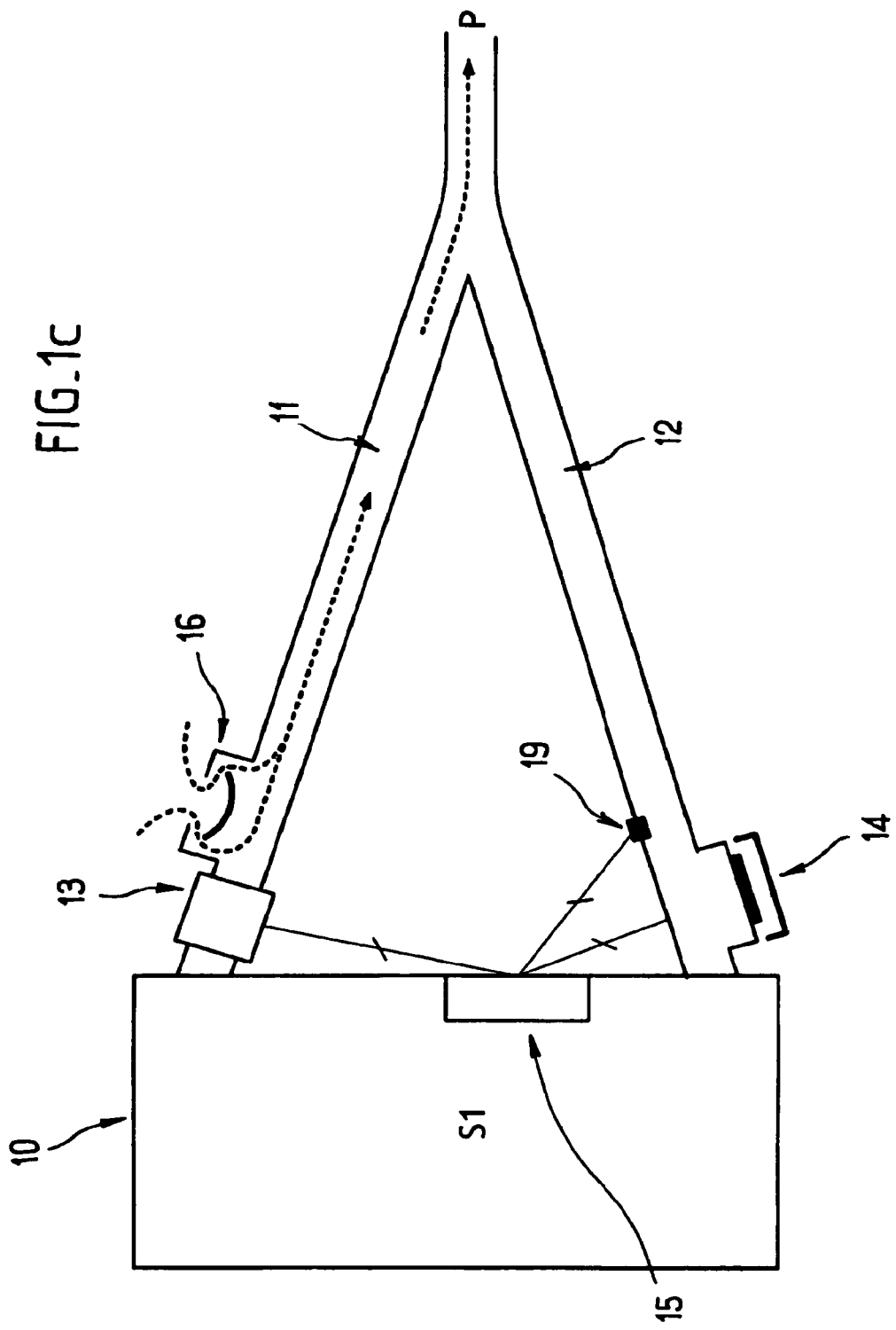

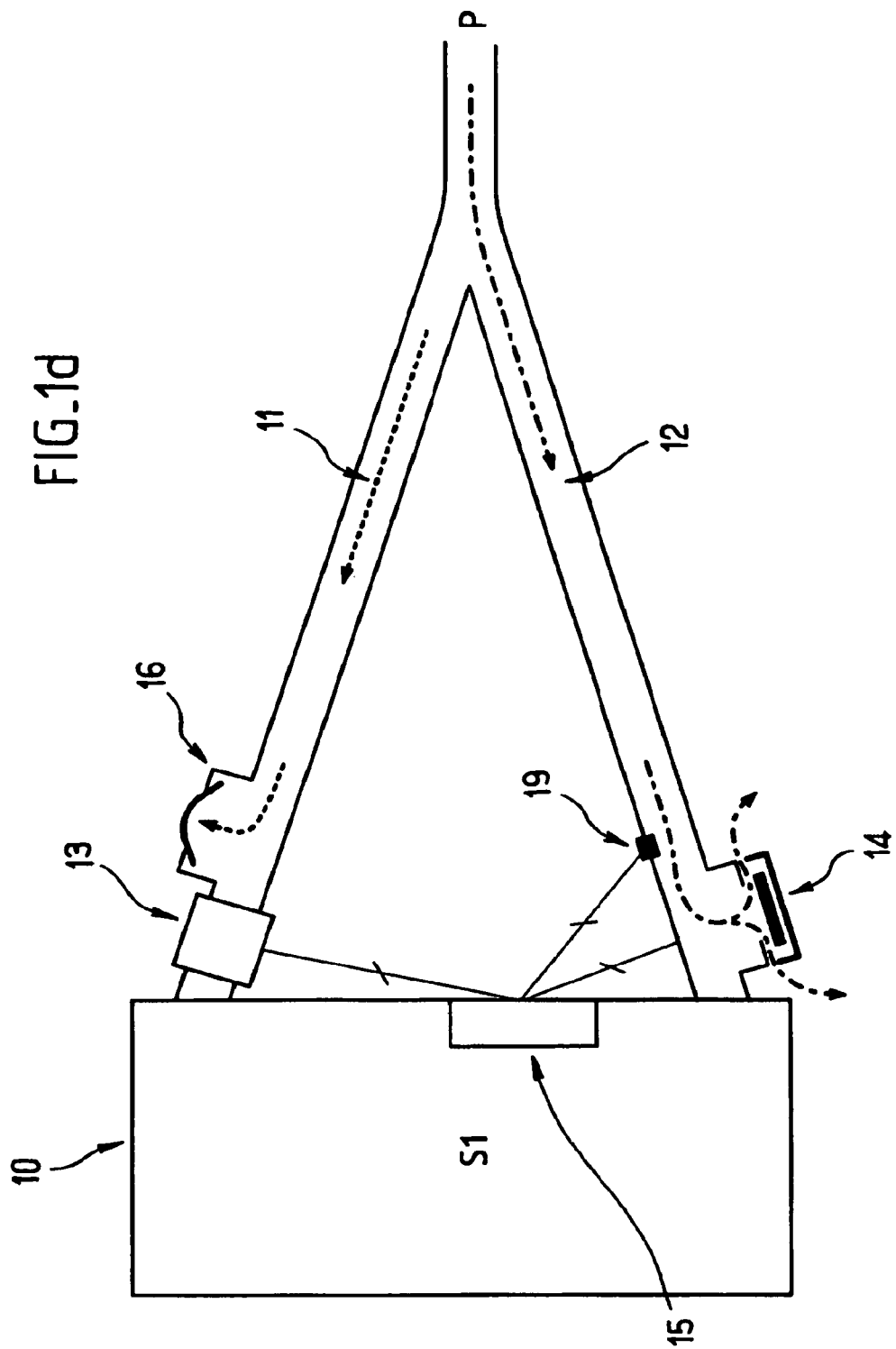

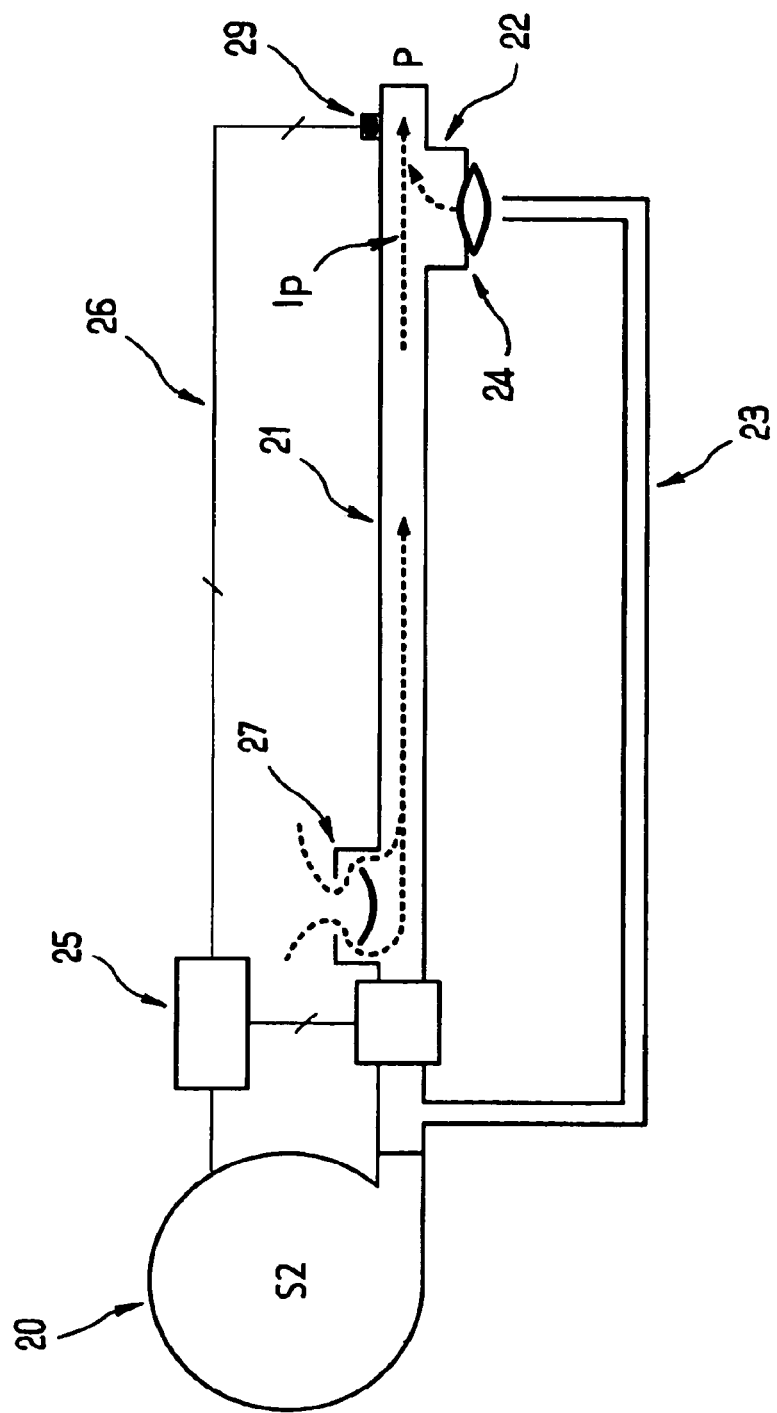

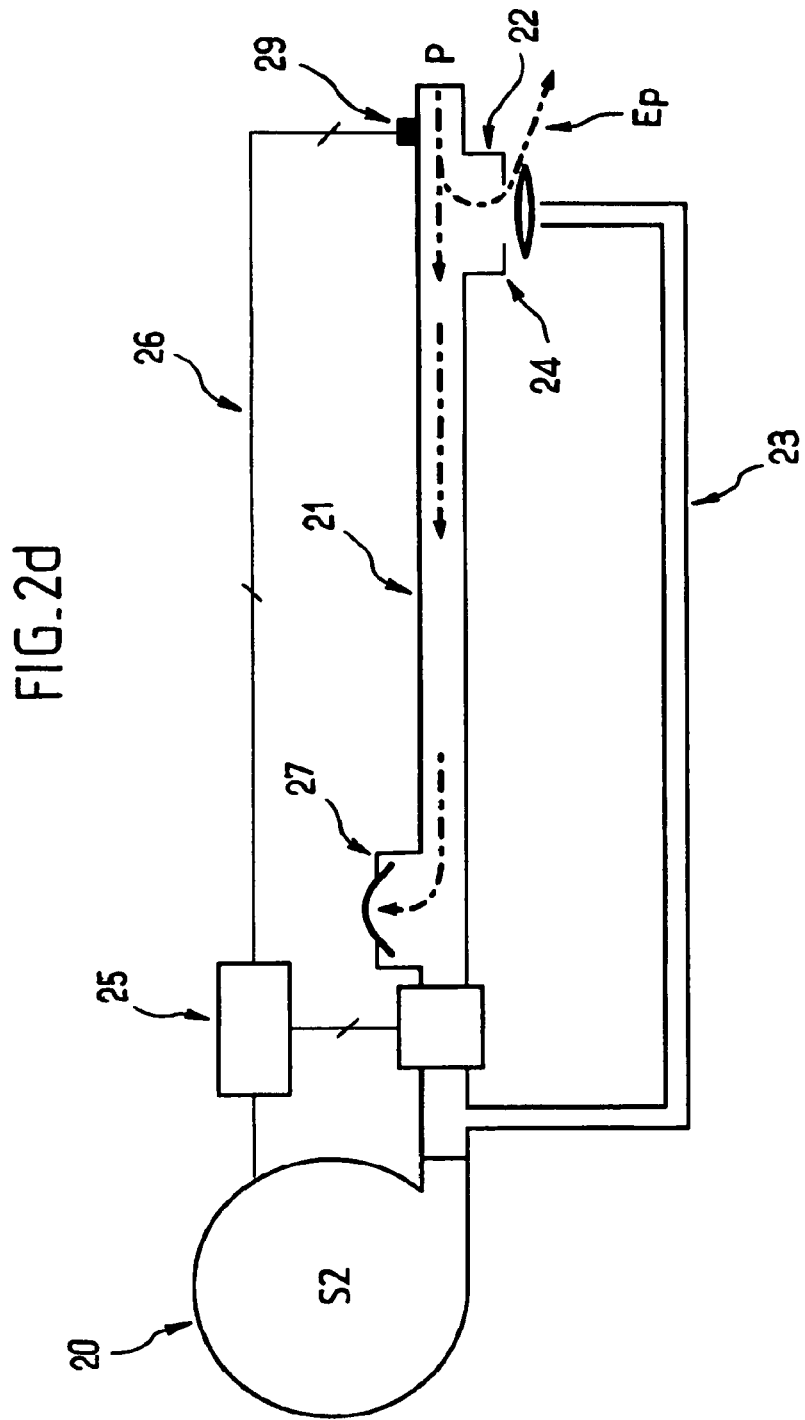

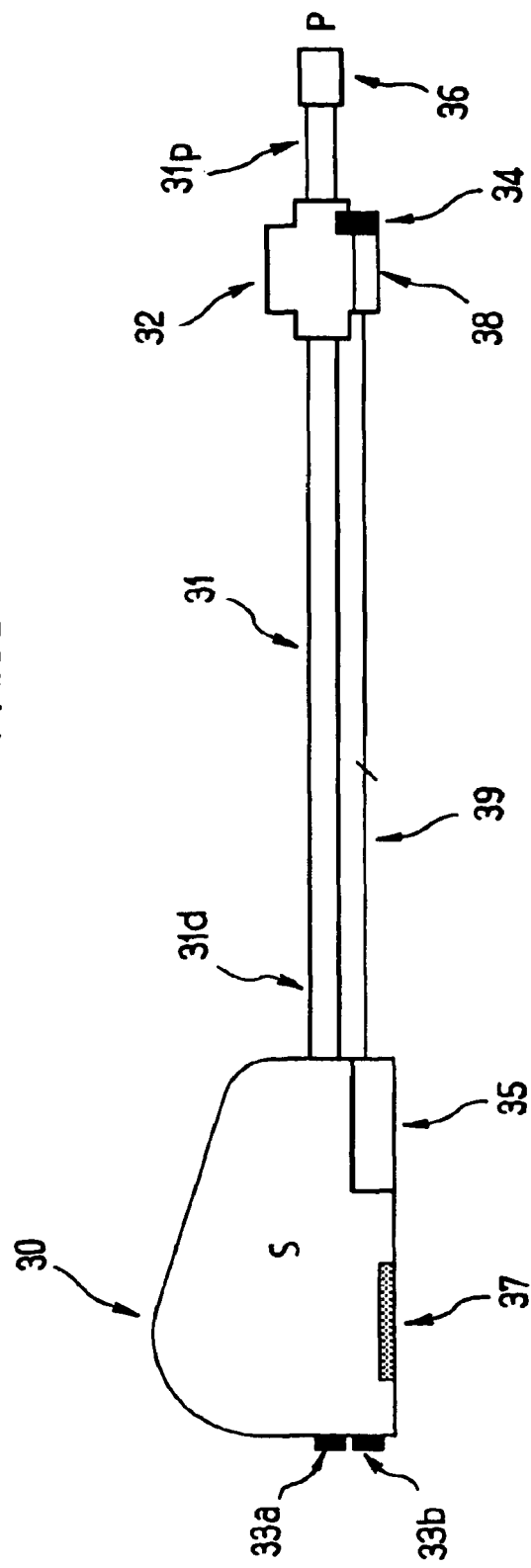

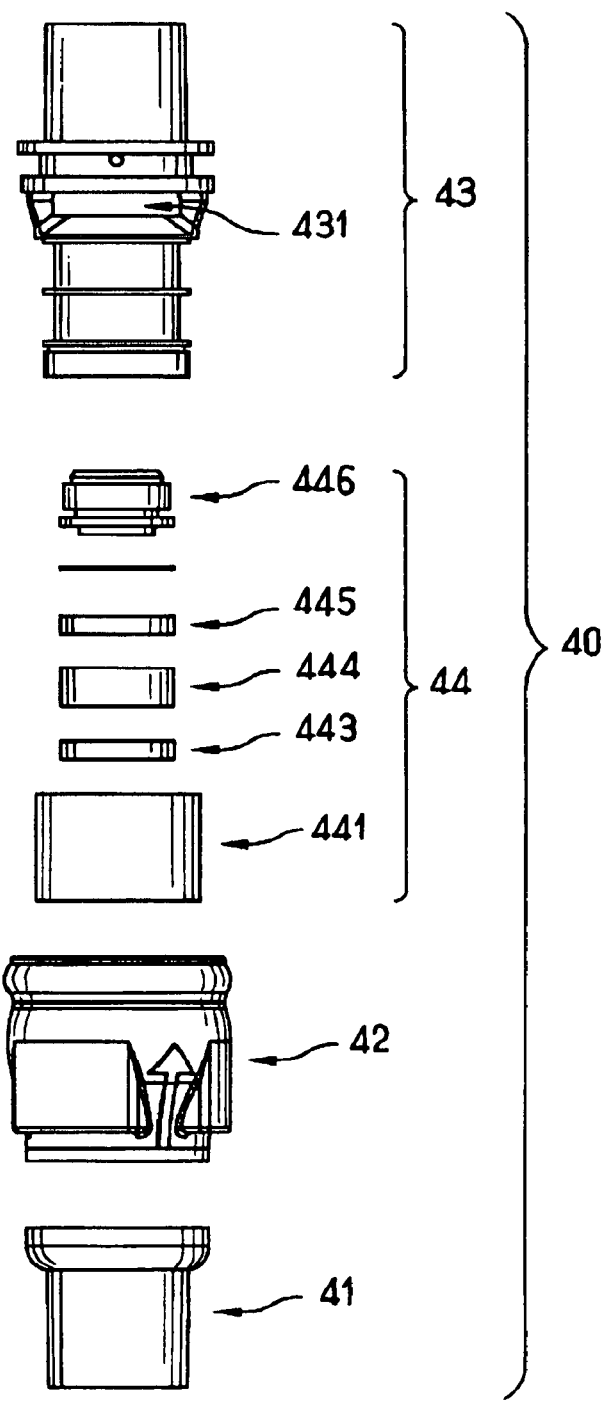

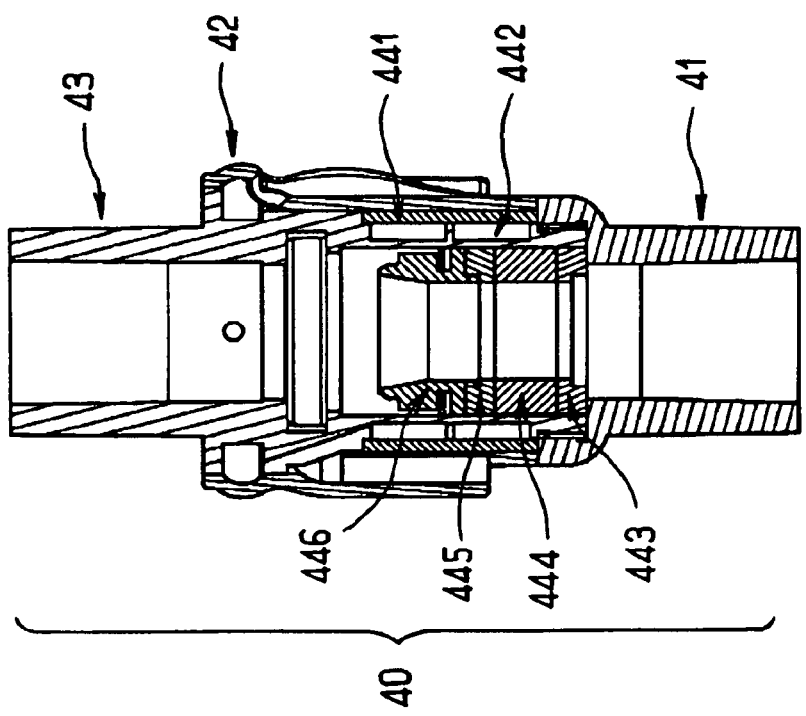

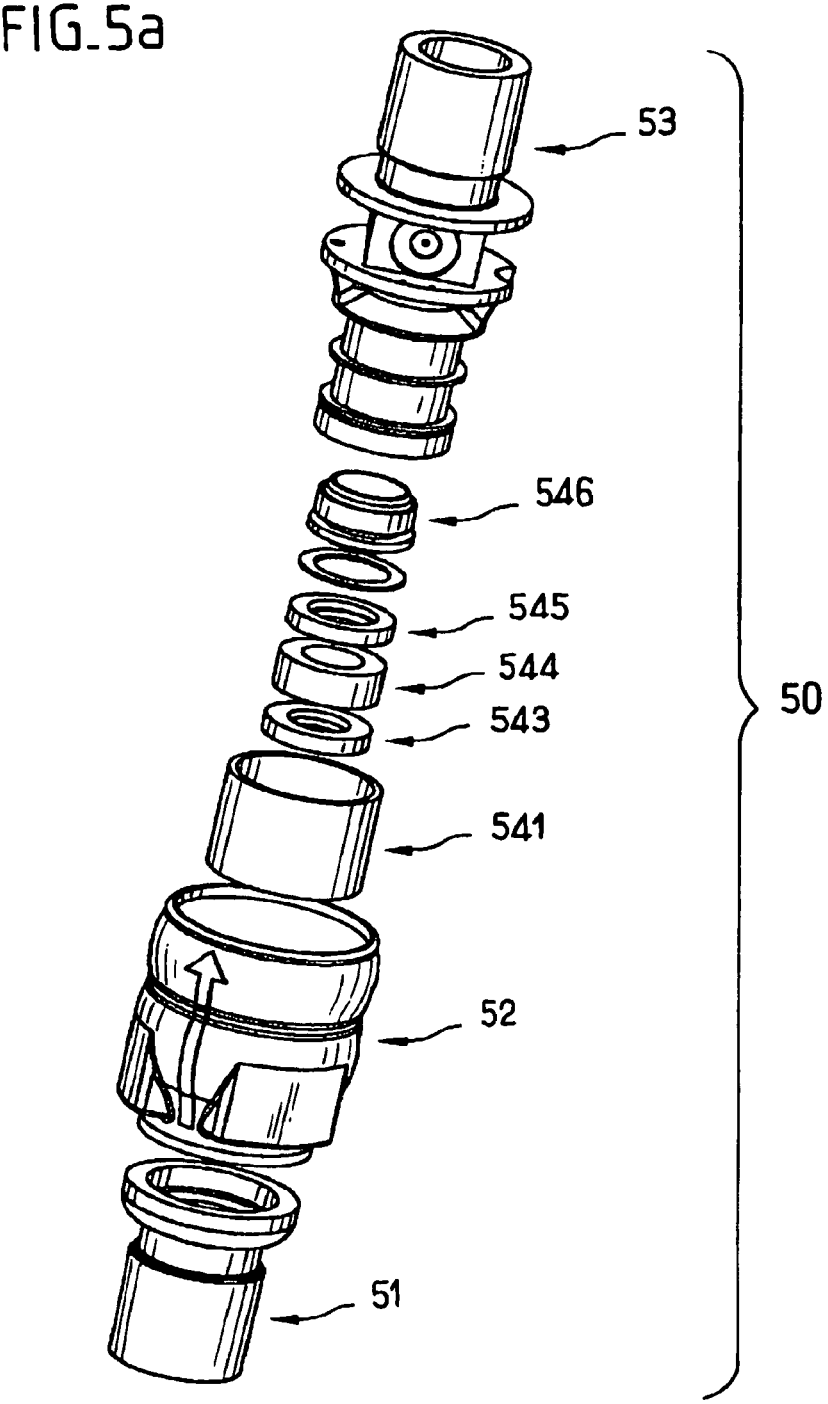

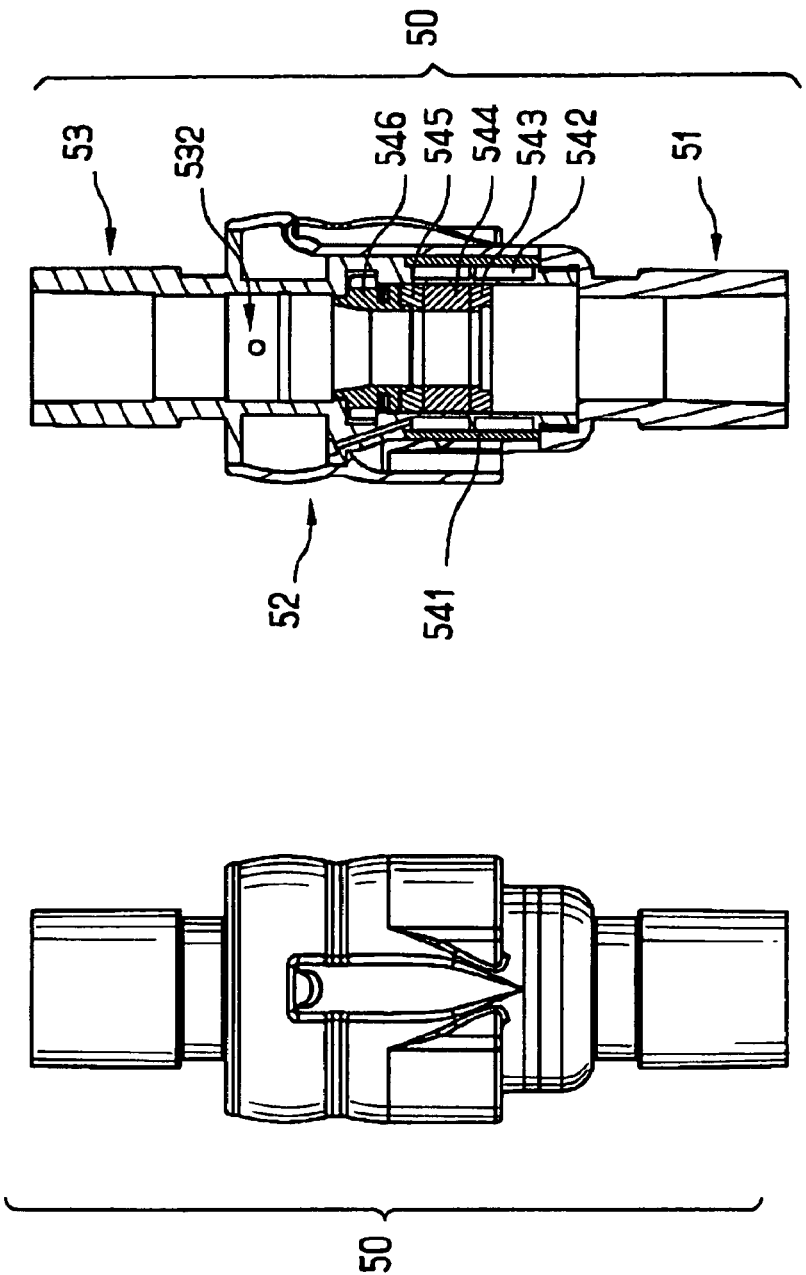

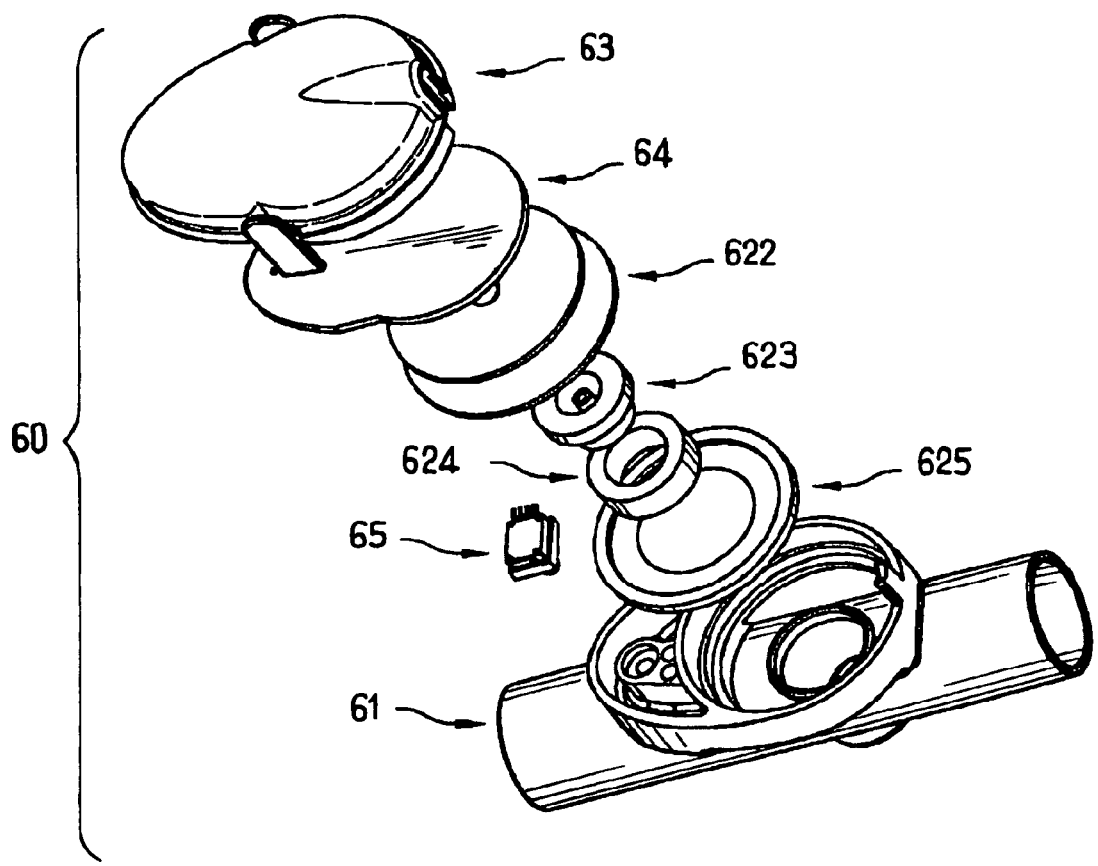
FIG_6a

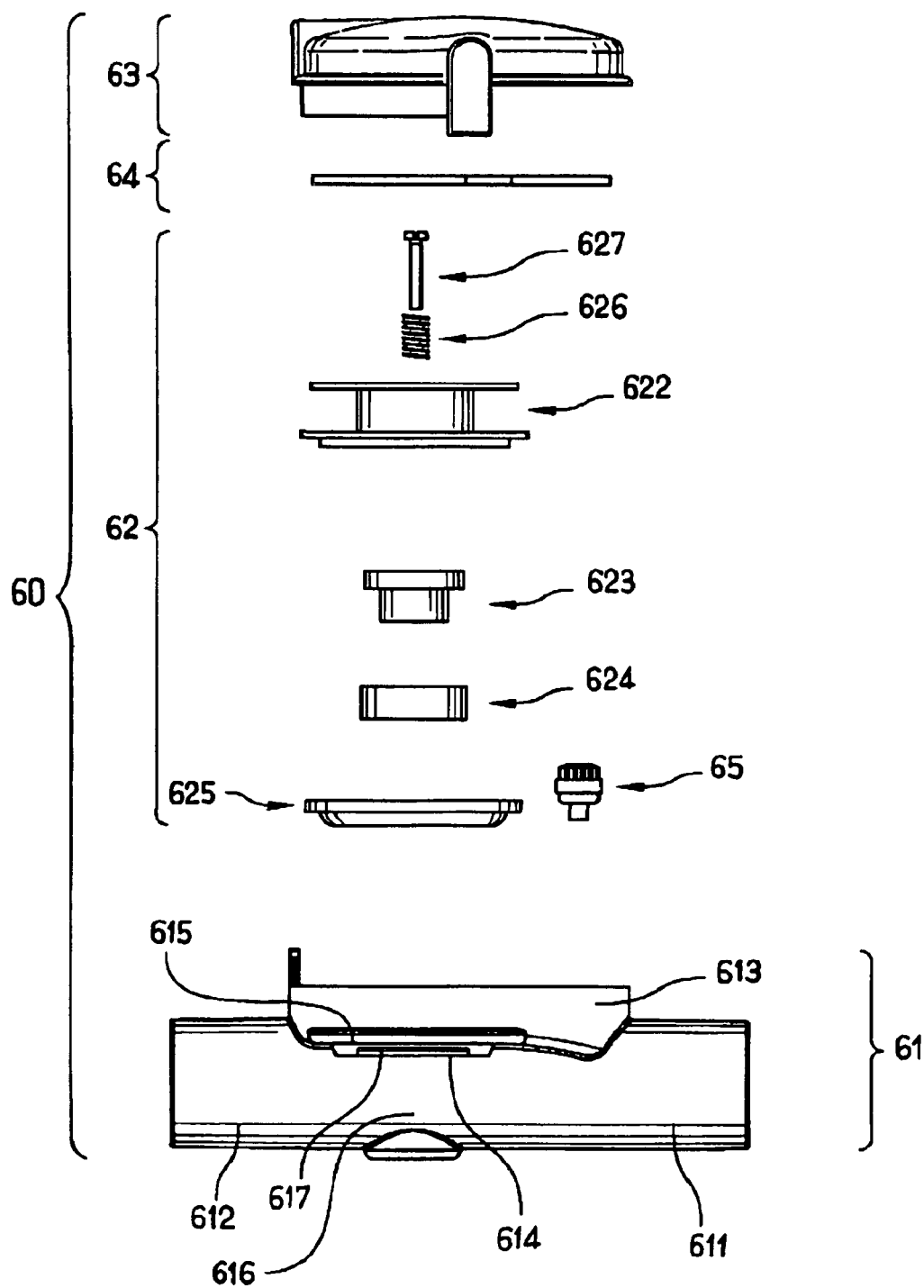

FIG_6d
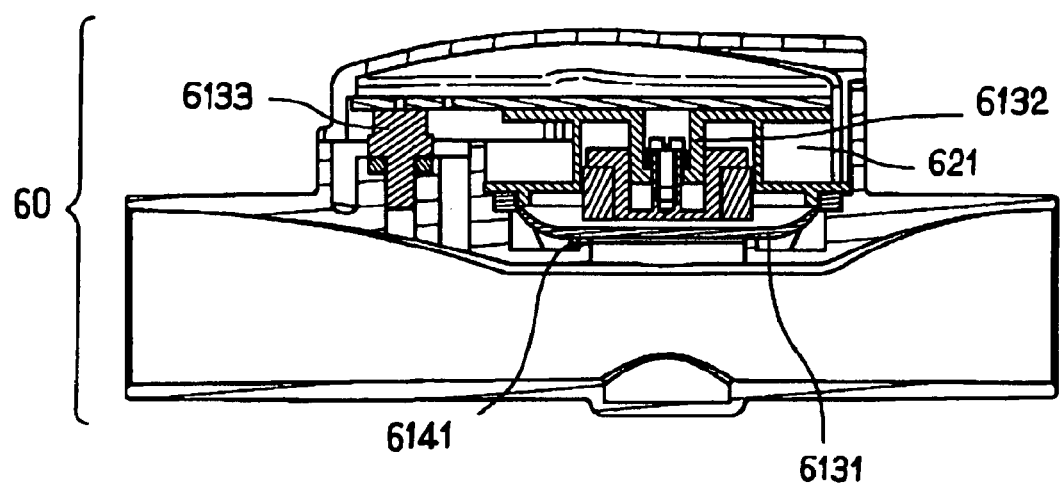

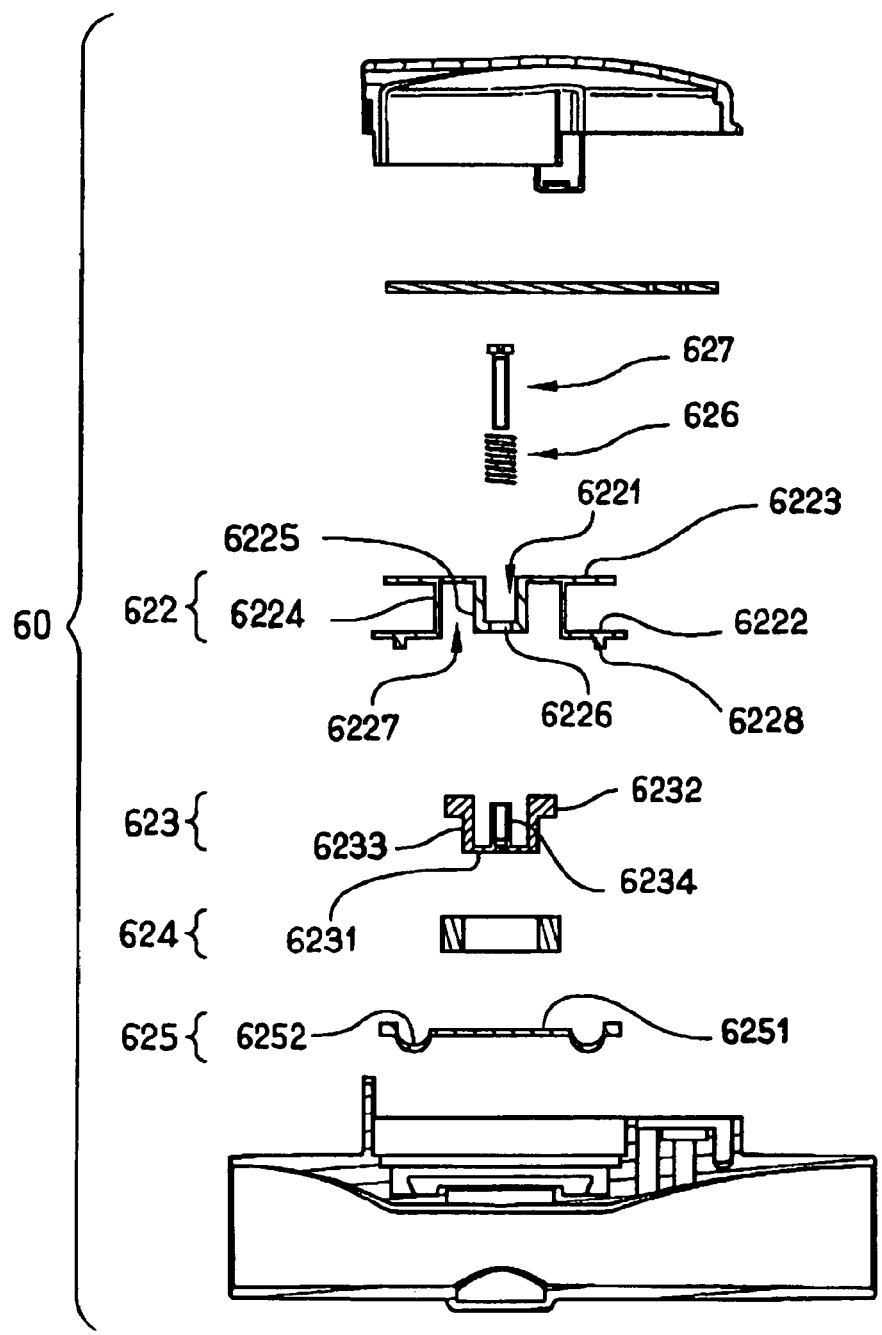
FIG_6f

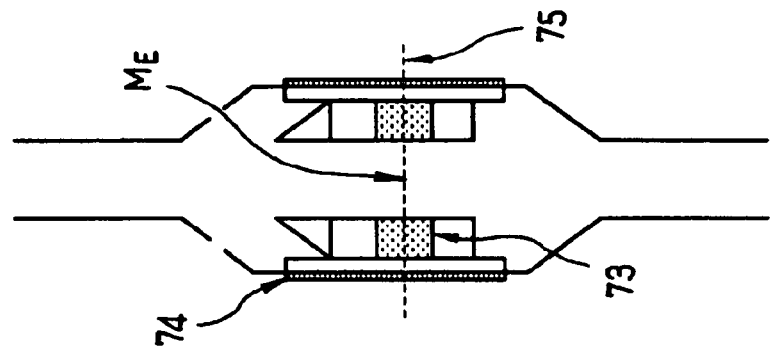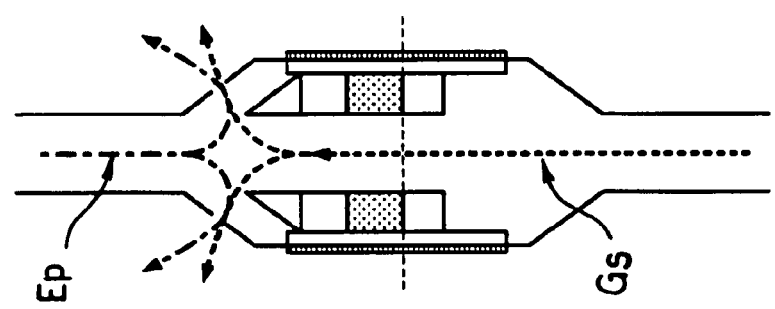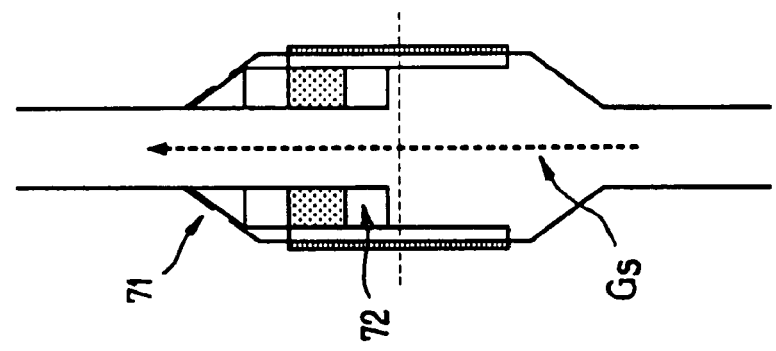

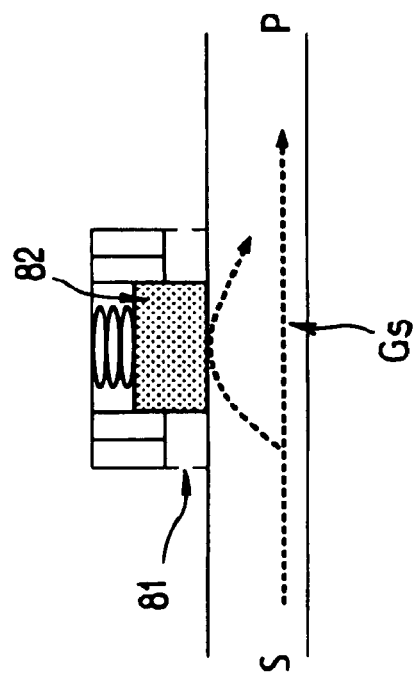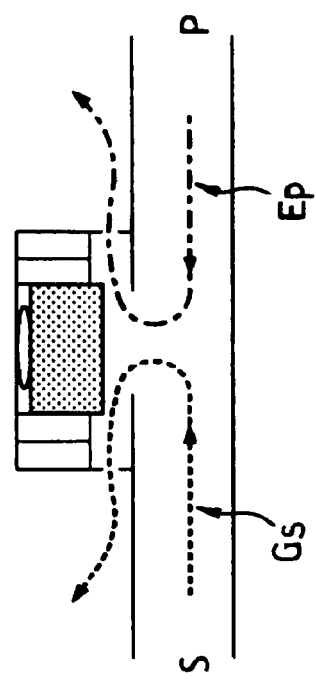

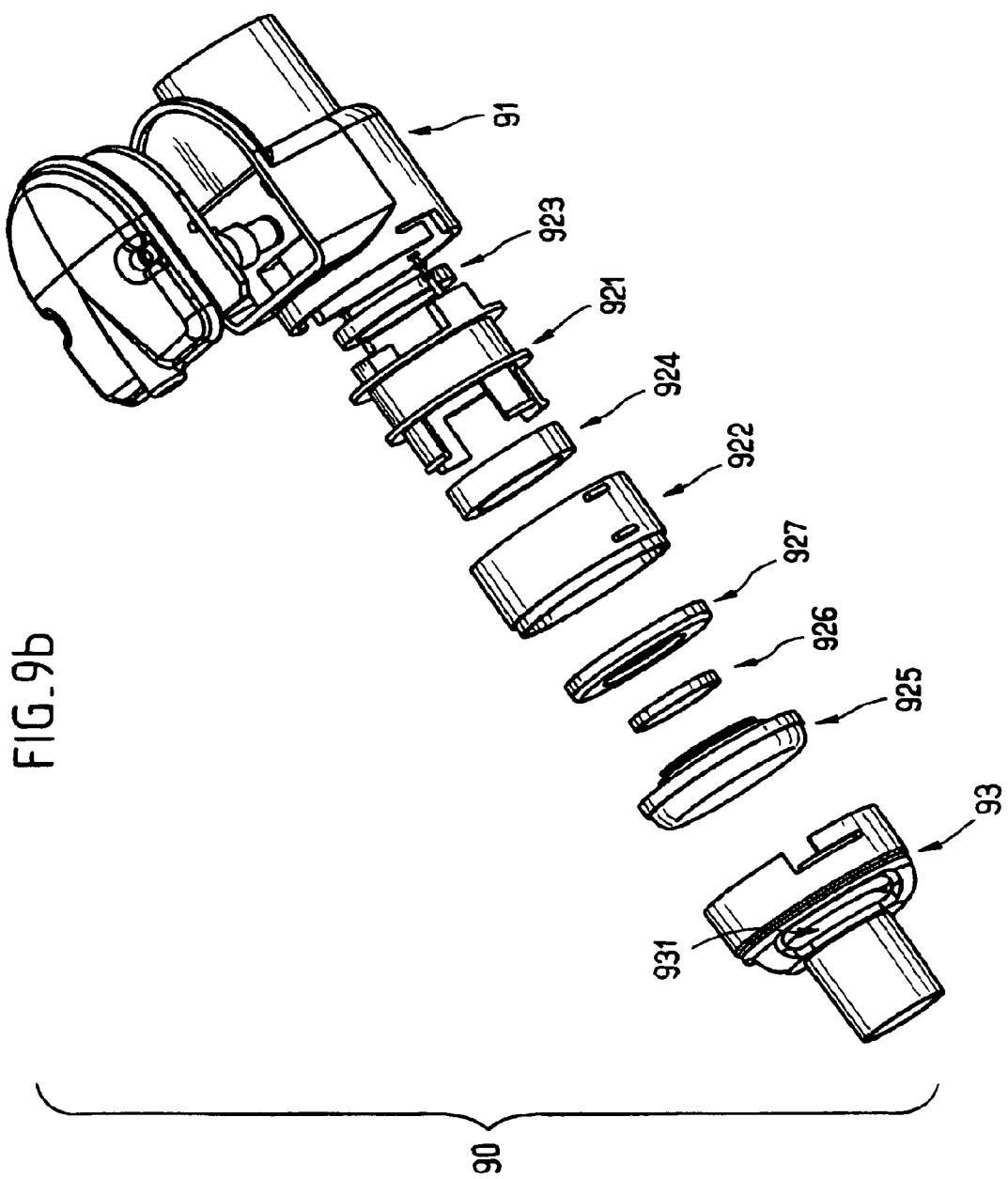

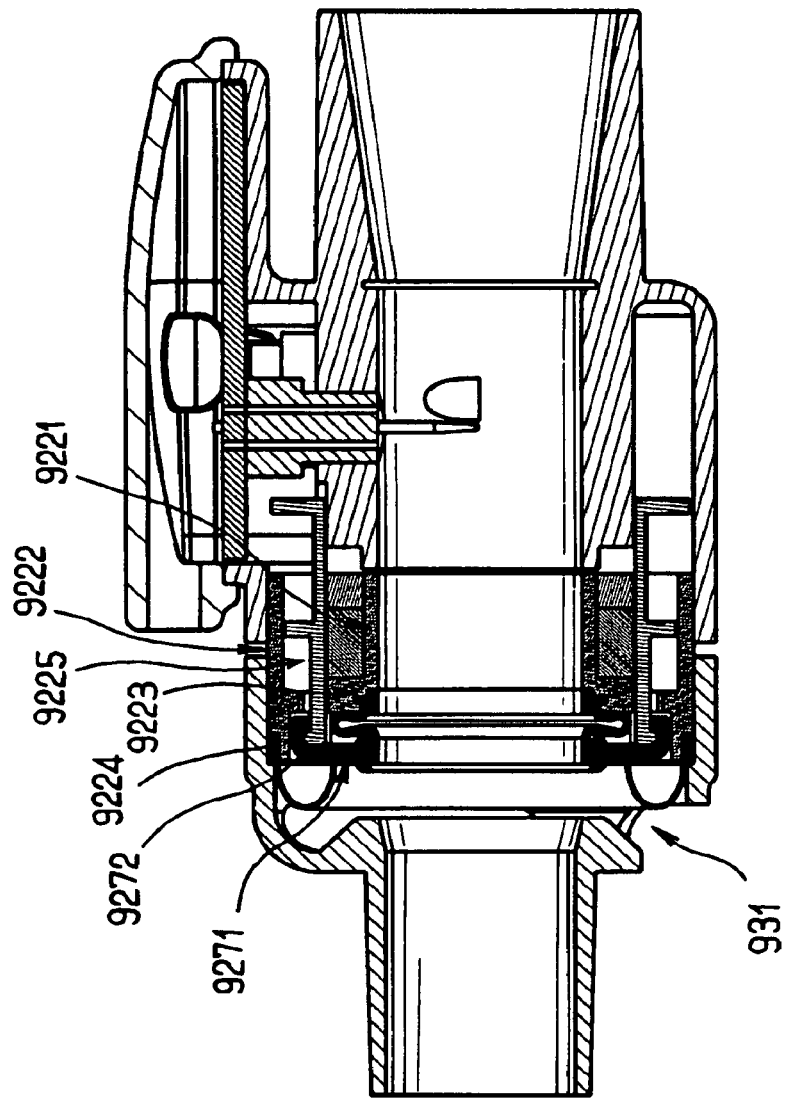

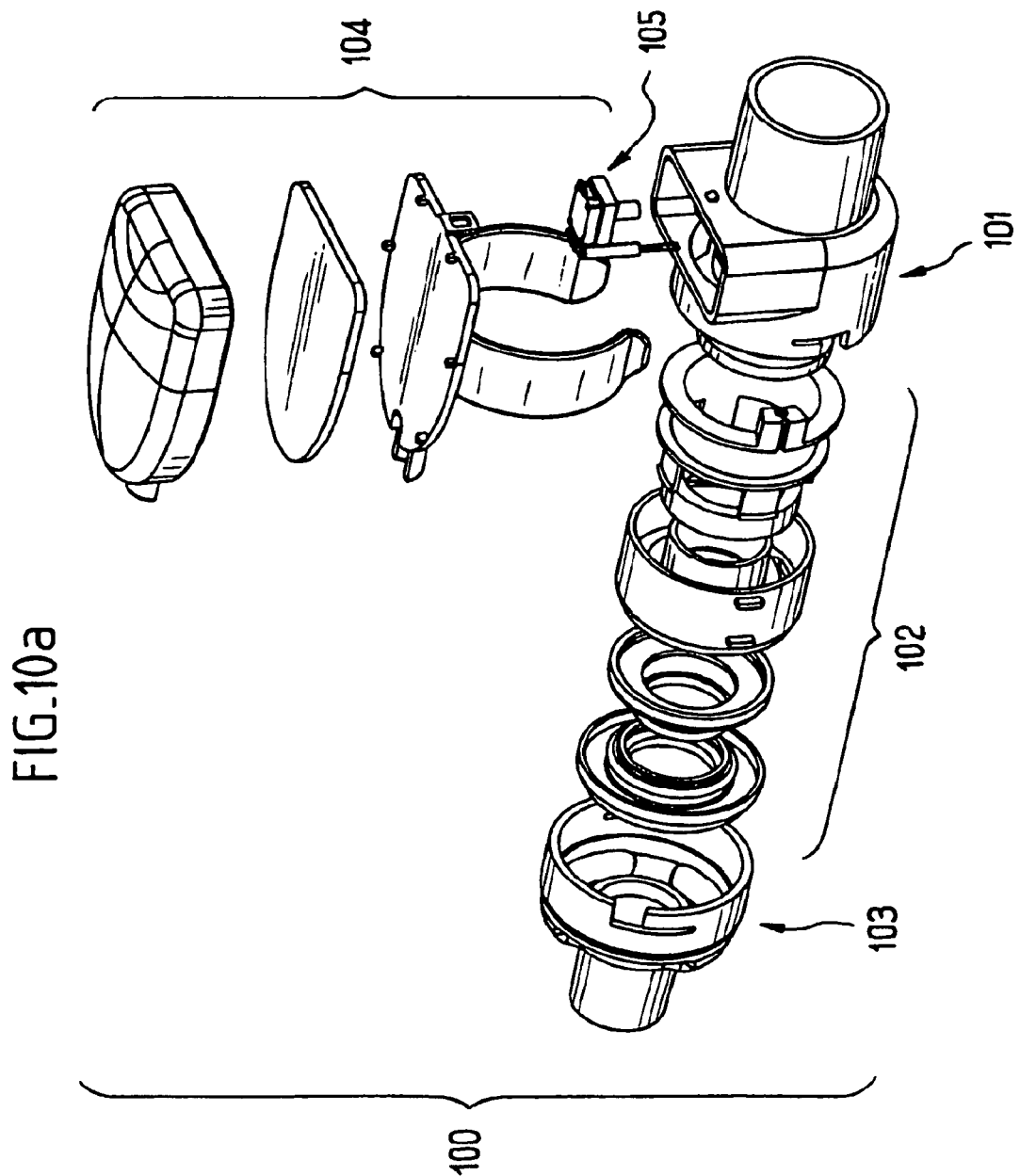

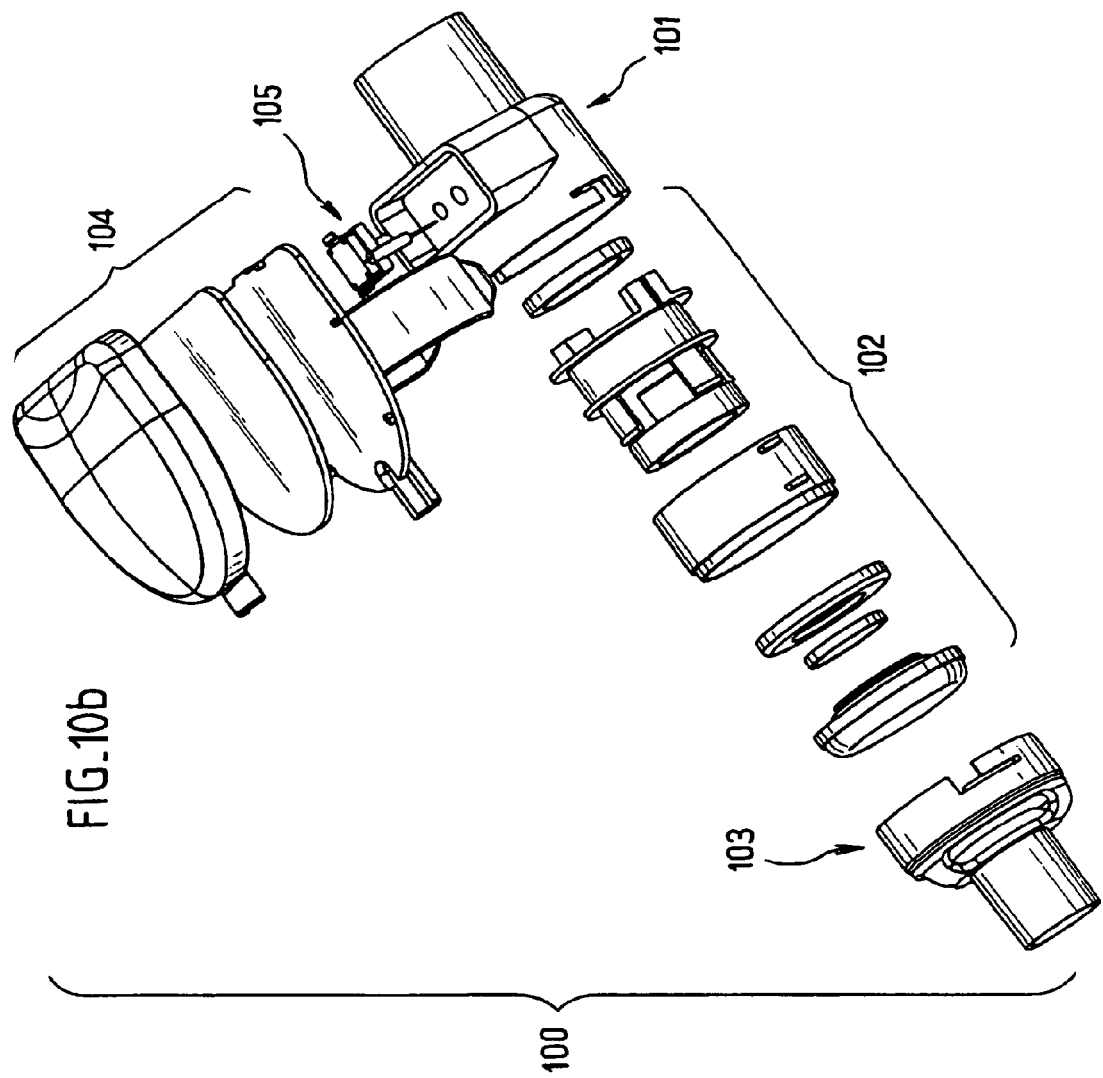

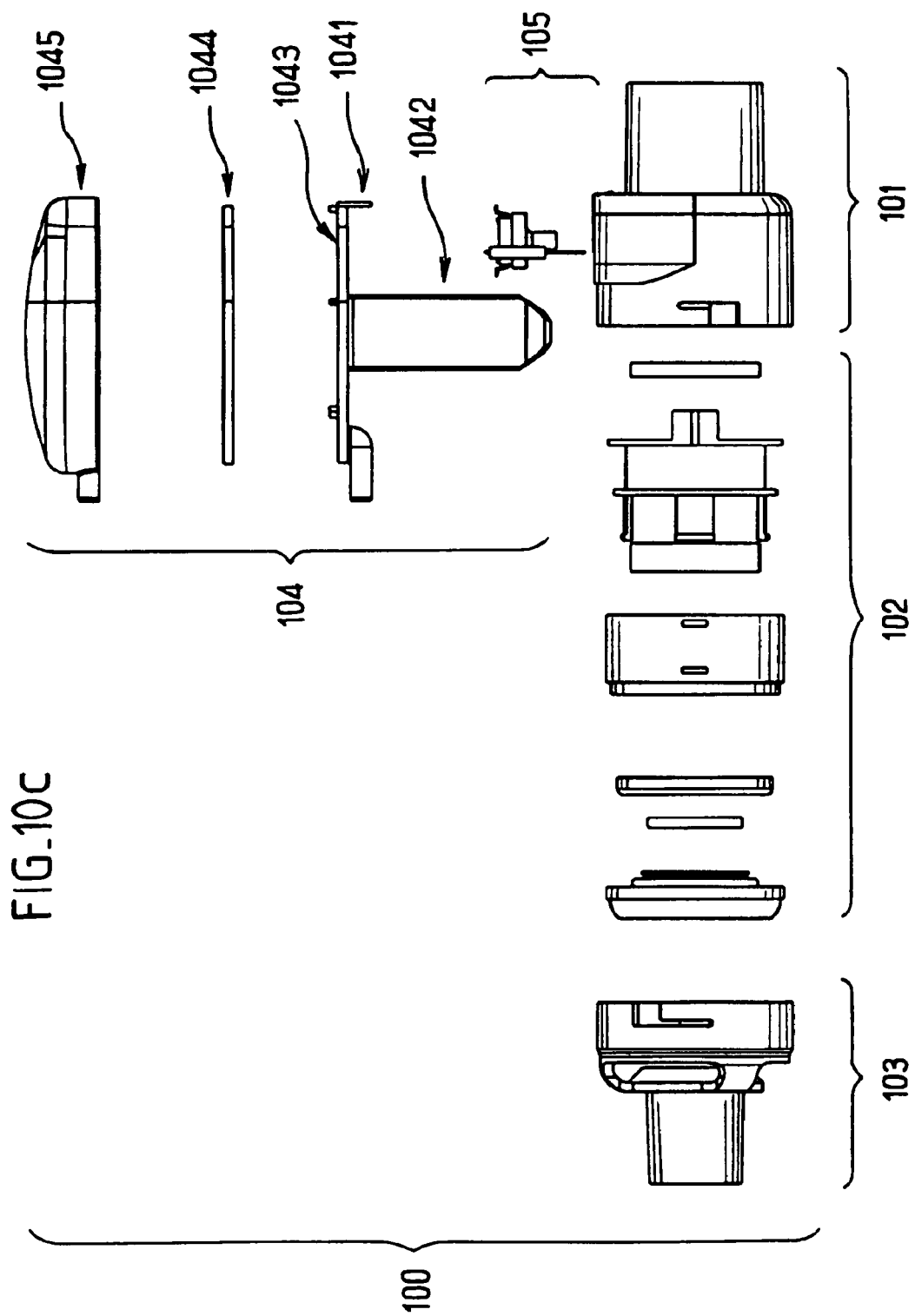

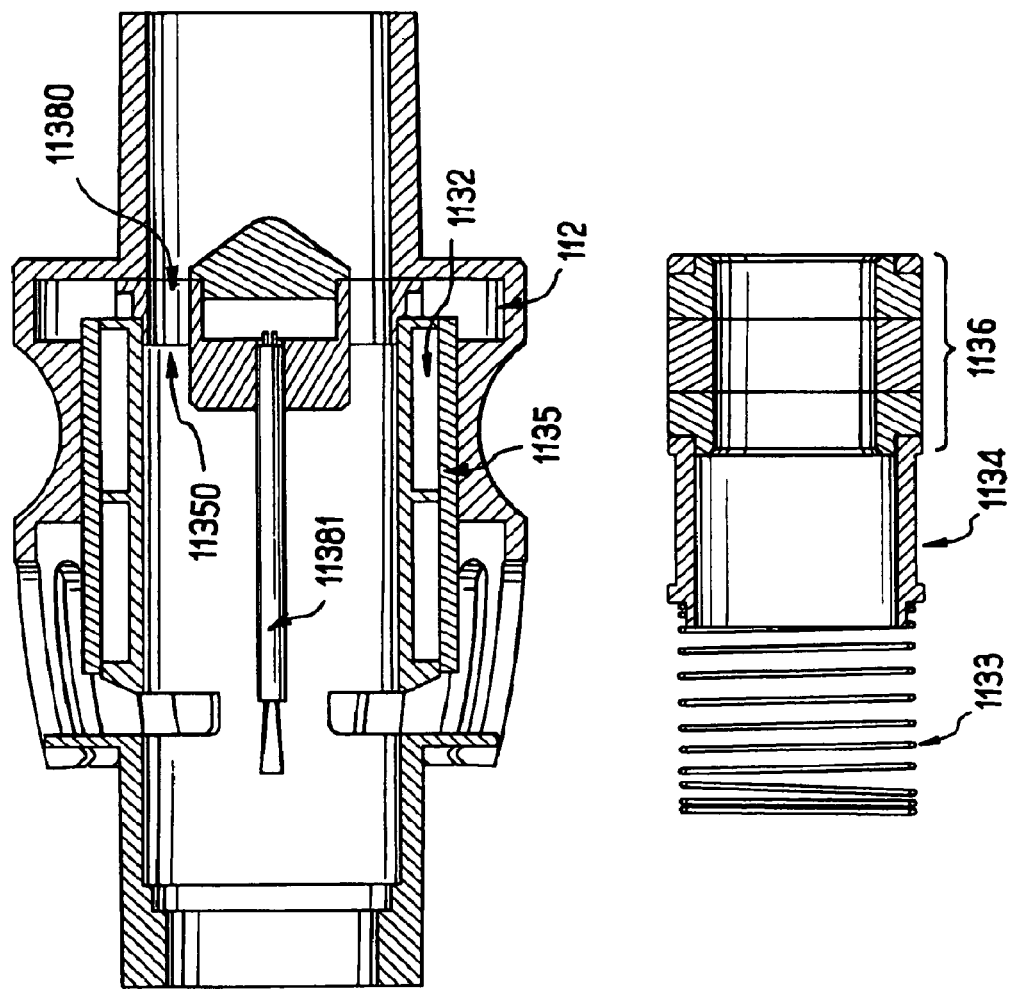

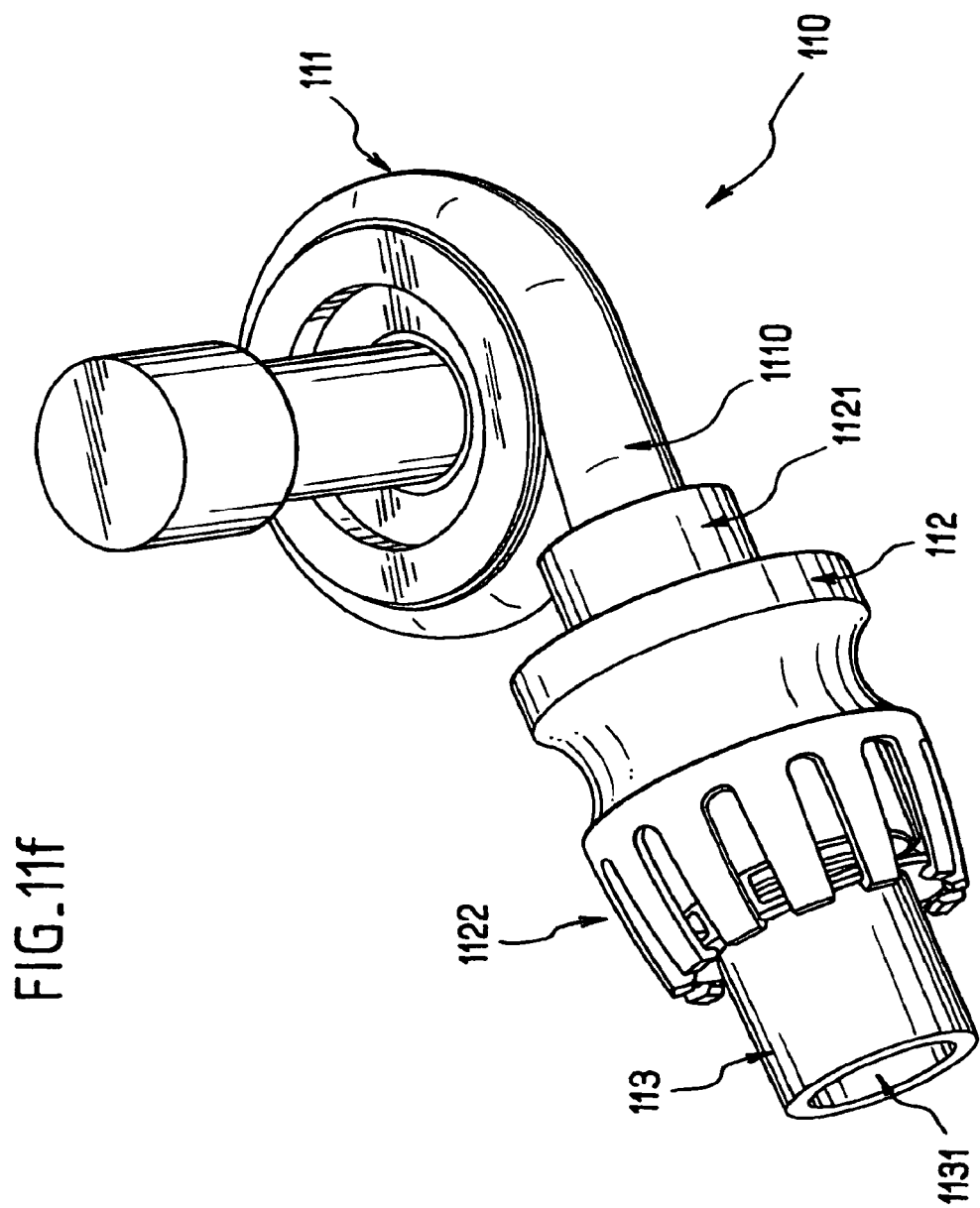

BREATHING ASSISTANCE DEVICE COMPRISING A GAS REGULATING VALVE AND ASSOCIATED BREATHING ASSISTANCE METHOD

CROSS-REFERENCE TO RELATED APPLICATIONS

The present application is a continuation of U.S. patent application Ser. No. 11/919,463, filed on Jun. 16, 2009, which application is a national phase entry under 35 U.S.C. §371 of International Application No. PCT/EP2006/061989 filed May 2, 2006, which claims priority from PCT/IB2005/001454 filed May 2, 2005, all of which are hereby incorporated herein by reference.

FIELD OF THE INVENTION

The present invention relates to a breathing assistance device for a patient.

More precisely, the invention relates to a breathing assistance device for a patient breathing in successive respiratory cycles, each respiratory cycle being defined by at least an inspiration phase and at least an expiration phase.

BACKGROUND OF THE INVENTION

A variety of breathing assistance devices, which we will also generally refer to as "respirators" in this text, are available today.

These respirators are equipped with a source of respiratory pressurized gas. They are qualified as "autonomous" as an external pressurized gas feeding is not required to operate them.

These devices provide the patient, at each inspiration, with a respiratory gas (typically ambient air to which a complementary gas such as oxygen can be added).

Different types of respirators are known. These different types of respirators can be classified e.g. according to their size.

Indeed, the size of these devices is an important parameter: it is generally desirable to minimize this size, in order to facilitate the operation of a same and single device in varied places and circumstances (e.g. home, as well as hospital), and in order to increase the mobility of the patient.

Non-Transportable Devices

A first type of respirators relates to the ones qualified as being non-transportable. This first type is schematically illustrated in FIGS. 1a to 1d.

Such devices are generally equipped with a respiratory gas source S1 having a very large size and/or weight. This gas source can be internal to the device, located in this case in a central unit 10, as the non-transportable respirator described hereinafter and illustrated in FIGS. 1a to 1d. The gas source can also be external to the device.

In these devices, the source of gas is coupled to the patient P through two ducts, an inspiration duct 11 dedicated to the inspiration phase and through which the patient P inspires the pressurized gas from the source of gas, and an expiration duct 12 dedicated to the expiration phase and through which the patient can exhale expiratory gases, such as carbon dioxide.

These non-transportable respirators are further provided with an inspiratory valve 13 and an expiratory valve 14. These two valves are located close to the gas source S1, respectively on the inspiration duct 11 and on the expiration duct 12.

The inspiratory valve 13 allows controlling the flux of the pressurized gas transmitted to the patient during the respiratory phases.

The expiratory valve 14 allows the expiratory gases of the patient to pass out of the expiratory duct 12, in the surrounding atmosphere. For this purpose, the expiratory valve can further be controlled with a PEP (Positive Expiratory Pressure).

Most of the operating modes of the respirators require a monitoring of the expiratory gas flow and/or expiratory pressure. Therefore sensor(s) 19 for sensing the gas flow and/or pressure have to be provided in the respirator.

Each sensor usually needs to be connected to the central unit 10 of the respirator by at least three wires, in order to be supplied with power and to convey data.

Therefore the sensors 19 are generally located near the gas source S1 in order to avoid further increasing the complexity of the already quite complex and large double transmission circuit by the addition of sensors and wires.

If it is desired that the sensors 19 are located in the vicinity of the expiratory valve, said expiratory valve 14 has thus to be located close to the gas source S1.

Both the inspiratory and expiratory valves require specific and often complex controlling means 15, i.e. controller 15, in order to be operated properly.

The non-transportable respirators are generally provided with relatively long ducts, of about 150 to 180 cm.

This configuration results in a high breathing resistance which increases the work of breathing of the patient.

Indeed, if the expiratory valve 14 is located at the end of the expiration duct 12 near the gas source S1 (distal end), and the expiration duct 12 being relatively long, the patient P will need to "push" his expiration through the expiration duct 12 until the expired air reaches the expiration valve to be vented to the atmosphere.

Transportable Respirators

A second type of respirators can be referred to as transportable respirators, as schematically illustrated in FIGS. 2a to 2d. This type of transportable respirator is provided with a central unit 20 comprising an internal respiratory gas source S2.

The gas source S2 may be a small turbine or blower, having optimized characteristics in order to limit the volume occupied by the device.

A further way to limit the volume of these devices is to use a single gas transmission duct 21 between the source S2 and the patient P, in contrast with devices having two ducts (an inspiration duct and an expiration duct).

The operation principle of these respirators is based on the use of an expiratory valve 22 located on the single duct 21, near the patient P (i.e. at the proximal end of the duct).

Such proximal localization of this expiratory valve 22 allows, in particular during the expiratory phase, to avoid the breathing resistance phenomenon which would be caused by the length of the duct used for expiration if the expiratory valve was located at the distal end of the duct.

In the known transportable respirators, such as represented in FIGS. 2a to 2d, this expiratory valve 22 is a pneumatic valve being operated thanks to a pressurized air feeding conduit 23, coupled with the respiratory gas source S2 (or to another source of pressure such as an independent microblower), and which inflates an obstructing cuff 24 of the expiratory valve 22.

Such control of the expiratory valve thus requires a specific conduit 23, which limits the miniaturization of the respirator.

During the expiration phase, the expiratory valve 24 is either opened or partially closed in order to establish a positive expiratory pressure (PEP) in the gas transmission duct to balance the residual overpressure in the patient lungs.

In order to establish such a PEP, it is necessary to control very precisely the pneumatic inflating pressure of the cuff 24 of the expiratory valve 22. This increases the complexity of the controller 25 of the respirator.

In some respiratory modes, the expiratory valve has to be operated as much as possible in real time, which is quite difficult in such expiratory valves because of the pneumatic inertias which are associated with them.

Moreover the configuration of such a known respirator imposes a limitation of the value of the PEP at around 20 mBar, while some respiratory modes would need a higher value of the PEP (e.g. 40 mBar or even more).

For the same reason as for non-transportable respirators, the expiratory gas flow and/or expiratory pressure may have to be controlled and gas flow and/or pressure sensors 29 have therefore to be provided near the expiratory valve 22.

Here again this requires providing wires along the gas transmission duct 21 between the central unit 20 containing the gas source S2 and the patient P (namely three wires—two for power supply and one for data transmission—for each pressure sensor, and two power supply wires for each gas flow sensor). Since expiratory gas flow and pressure generally have to be measured, a connection cable 26 of at least five wires is thus required between the central unit 20 and the expiratory valve 22 at the proximal end of the device.

Comment on Situation of Disabled Control of the Expiratory Valve

In order for the patient to safely use a respirator, the latter being transportable or not, this device must of course allow the patient to breathe in any situation, including if the pressurized gas source is disabled (breakdown or other). There are therefore safety standards to fulfil so that the breathing assistance device can work even if the gas source is disabled.

Thus, with a respirator having a single gas transmission duct 21 as described before and a specific conduit 23 for pneumatic control of the expiratory valve 22, the patient P can always expires through the pneumatic expiratory valve 22, even if the pneumatic feeding of the expiratory valve 22 is disabled, as shown in FIG. 2d.

Indeed, if the pneumatic feeding of the expiratory valve is disabled, (this being the case when the gas source is disabled, if the source provides the control of the valve), the cuff 24 of the expiratory valve 22 will not be fed anymore, preventing therefore the PEP control, but still allowing the patient P to reject the expiratory gases $E_P$ through the expiratory valve 22.

In such case, it will however be impossible for the patient P to inspire through this pneumatic expiratory valve 22, since the cuff 24 shall obstruct the passage between the inside and the outside of the transmission duct 21, because of the patient inspiration $I_P$.

Consequently, transportable respirators as illustrated in FIGS. 2a to 2d comprise a safety back flow stop valve 27 near the gas source S2. As represented in FIG. 2a, this safety valve 27 will normally be closed under the effect of the pressure feeding $G_S$ coming from the gas source S2, but if the latter is disabled, the pressure of the patient inspiration $I_P$ will open the safety valve 27, allowing the patient P to inspire air from outside, as illustrated in FIG. 2c.

The disabling of the gas source S2 corresponds to a particular case of disabling of the pneumatic control of the expiratory valve 22. It is specified that in this text such disabling of the gas source S2 is understood as more generally referring to a disabling of the pneumatic control of the expiratory valve 22.

In order to allow a safe inspiration through the safety valve 27 and the whole length of the duct 21, the diameter of the duct will have to be large.

It is specified in this respect that there are generally pressure loss standard requirements to fulfil for addressing this issue of safety. For example, the French standards state that the maximum pressure loss between the source and the patient must not exceed 6 hPa for 1 liter•second for an adult and 6 hPa for 0.5 litre•second for a child.

And in order to fulfil such requirements, the transmission duct of known devices such as illustrated in FIGS. 2a to 2d must have a minimum diameter of 22 mm for an adult and a minimum diameter of 15 mm for a child.

Such large diameter of the duct is of course an obstacle to miniaturization of the device.

For a non transportable respirator (see FIGS. 1a to 1d), the patient P will always be able to expire through the expiration duct 12, even if the gas source S1 is disabled, as shown in FIG. 1d.

If the gas source S1 is disabled, as illustrated in FIG. 1c, the inspiration phase is made possible through a safety back flow stop valve 16 located on the inspiration duct 11, near the gas source S1.

This safety back flow stop valve 16 is not located on the expiration duct 12 as it would be dangerous for the patient P to inspire through the expiratory duct 12 which contains a plug of carbon dioxide.

For the same reasons as for the transportable respirators, the diameters of the duct must be relatively large to fulfil the pressure loss requirements, that is a least 15 mm for children and 22 mm for adults, in order to allow a safe inspiration through the safety valve 16.

And here again, such large diameter is an obstacle to miniaturization.

Comment on Ability to Operate According to Different Modes

In addition, it is to be noted that the pathologies and diseases to be treated by the respirators are varied, and the breathing assistance devices can therefore be of different types, such as pressure-controlled or volumetric-controlled, and be operated according to different operating modes.

Each operating mode is defined by particular setting and checking variables but also by a particular type of material.

Some devices, which can be referred to as hybrid, are able to work according to several operating modes. However their material configuration, in particular the accessories (as the type of ducts between the gas source and the patient, the presence or not of an expiratory valve, the use of a mask with apertures, etc.), must be adapted to the chosen operating mode. And it would be desirable to operate a same and single device according to a large variety of modes, without requiring adapting the device (i.e. adapting its ducts, accessories, etc.).

Generally, it is an object of the invention to address one or more of the limitations and drawbacks mentioned above in this text.

BRIEF SUMMARY OF THE INVENTION

A first aspect of the invention is to allow miniaturization of a respirator device.

In one form of the invention the diameter of a duct between a source and a patient is reduced, while fully respecting the safety requirements.

It is a further aspect to provide a simple configuration. In one form the number of wires between the central unit of the respirator and the proximal end of the duct is reduced.

Another aspect is to allow real-time control of the device. In one form of the invention real-time control of a gas regulation valve of a device is provided.

A further aspect of the invention is to allow multiple operating modes within a single respiratory device, without requiring adaptation of the device.

In one form the invention relates to a breathing assistance device as recited in claim 1.

In particular, the invention concerns a breathing assistance device for a patient breathing in successive cycles, each cycle being defined by at least an inspiration phase and at least an expiration phase, said breathing assistance device including:
- a source of respiratory pressurized gas,
- a gas transmission duct comprising a distal end coupled to said source and a proximal end coupled to said patient,
- a gas regulating valve comprising at least a leakage orifice between the inside and outside of said duct, and an obstruction element capable of varying the opening of said leakage orifice upon signal of a controller, characterized in that the gas regulating valve is interposed in said duct at a proximal location, and that the obstruction element is capable of allowing a bidirectional gas flow through said leakage orifice in both expiration and inspiration phases.

Preferred but not limited aspects of such a breathing assistance device are the following:
- the obstruction element is electrically controlled, and the obstruction element may be an electromagnetic obstruction element;
- the obstruction element includes a return so that the leakage orifice remains at least partially opened in the absence of signal from the controller;
- the return is a magnetic equator;
- the electromagnetic obstruction element includes a metallic sheath wherein a coil is fixed, said coil being controllable by the controller and surrounding a movable magnetic element, the metallic sheath and the movable magnetic element defining the magnetic equator;
- the magnetic element comprises a toric magnet, a first polar piece and a second polar piece, said first and second polar pieces being coaxially fixed on either side of the toric magnet and being of different polarities, and said second polar piece comprising an obstruction piece being capable of obstructing the leakage orifice. The magnetic element is translatable along an axis of revolution of the toric magnet;
- the electromagnetic obstruction element may include two coaxial coils controllable by the controller, the first coil substantially surrounding the toric magnet and the first polar piece, and the second coil substantially surrounding the toric magnet and the second polar piece;
- the electromagnetic obstruction element is mounted coaxially relative to the gas transmission duct;
- the return is a compression spring;
- the electromagnetic obstruction element includes an armature surrounded by a coil, said coil being controllable by the controller, and said armature comprising an inner toric space wherein a magnetic element is translatable;
- the magnetic element is capable of obstructing the leakage orifice;
- the magnetic element is constraint by the compression spring;
- the magnetic element comprises a toric magnet and a magnet guide;
- the electromagnetic obstruction element is mounted transversally relative to the gas transmission duct.
- the return is a rubber membrane;
  - the rubber membrane comprises a bellows designed for maintaining the obstruction element in a position where the leakage orifice is at least partially opened;
  - the bellows is designed for enhancing the returning function if gas pressure within the valve increases;
  - the bellows has a convex curvature oriented towards walls of the valve;
  - the obstruction element is at least partially confined within an independent space from the duct.

Another aspect of the invention concerns a breathing assistance method for assisting a patient with a breathing assistance device of the invention, as defined in claim 17.

In particular, it concerns a breathing assistance method for assisting a patient with a breathing assistance device according to the invention, characterized in that the leakage orifice is at least partially opened in the absence of signal from the controller.

Preferable but not limited aspects of such a breathing assistance method are the following:
- the leakage orifice is totally obstructed during inspiration phases whereas it is a least partially opened during expiration phases;
- the leakage orifice, during expiration phases, is opened so that positive expiratory pressure (PEP) remains equal to expiration pressure of the patient;
- the leakage orifice is totally opened in case of breakdown of the source of respiratory pressurized gas.

The invention further relates to a gas regulating valve for a breathing assistance device, as recited in claim 25.

In particular, it relates to a gas regulating valve for a breathing assistance device, being interposed in a gas(transmission duct of said breathing assistance device at a proximal location, and comprising at least a leakage orifice between the inside and outside of said duct, and an obstruction element capable of varying the opening of said leakage orifice upon signal of a controller, characterized in that the gas regulating valve is capable of allowing both an inward or an outward gas flow in both expiration and inspiration phases.

Preferable but not limited aspects of such a gas regulating valve are the following:
- the obstruction element includes a return so that the leakage orifice remains at least partially opened in the absence of signal from the controller;
- the obstruction element is an electromagnetic obstruction element including a metallic sheath wherein a coil is fixed, said coil being controllable by the controller and surrounding a translatable magnetic element, the magnetic element comprising a toric magnet, a first polar piece and a second polar piece, said first and second polar pieces being coaxially fixed on either side of the toric magnet and being of different polarities, and said second polar piece comprising an obstruction piece being capable of obstructing the leakage orifice;
- the obstruction element is an electromagnetic obstruction element including an armature surrounded by a coil, said coil being controllable by the controller, and said armature comprising an inner toric space wherein a magnetic element is translatable, the magnetic element being capable of obstructing the leakage orifice and being constraint by a compression spring.

The invention further relates to a gas regulating valve for a breathing assistance device, as recited in claim 29.

In particular, it relates to a gas regulating valve for a breathing regulating device, comprising at least a leakage orifice to the atmosphere and an obstruction element capable of varying the opening of said leakage orifice upon signal of a controller, and passage means between the valve and a pressurized gas source, characterized in that said obstruction element can be moved between a position where it closes said passage means and a position where it closes said leakage orifice.

The invention further relates to a gas regulating valve for a breathing assistance device, as recited in claims 30 and 31.

In particular, it relates to a gas regulating valve for a breathing assistance device, comprising a casing provided with at least a leakage orifice, an obstruction element capable of varying the opening of said leakage orifice upon signal of a controller, and a processing portion (104) for connecting measurement means to the controller (35), characterized in that the processing portion is designed for being removably connected to the casing. The processing portion may namely comprise a clip designed for surrounding the casing so that processing portion may be removably clipped on the casing.

BRIEF DESCRIPTION OF THE DRAWINGS

Other features and advantages of the invention will become clear from the following description which is only given for illustrative purposes and is in no way limiting and should be read with reference to the attached drawings on which, in addition to FIGS. 1a to 1d and 2a to 2d which have already been commented above:

FIG. 3 is a schematic representation of a breathing assistance device according to the invention;

FIG. 4b is a plan exploded view of the gas regulating valve of FIG. 4a;

FIG. 4c is a side view of the gas regulating valve of FIG. 4a;

FIG. 4e is a sectional view of the gas regulating valve of FIG. 4a with an opened leakage orifice;

FIG. 5a is a three-dimensional exploded view of a gas regulating valve according to a second embodiment of the invention;

FIG. 5b is a plan exploded view of the gas regulating valve of FIG. 5a;

FIG. 5c is a side view of the gas regulating valve of FIG. 5a;

FIG. 5d is a sectional view of the gas regulating valve of FIG. 5a with a closed leakage orifice;

FIG. 6a is a three-dimensional exploded view of a gas regulating valve according to a third embodiment of the invention;

FIG. 6b is a exploded plan view of the gas regulating valve of FIG. 6a;

FIG. 6c is a side view of the gas regulating valve of FIG. 6a;

FIG. 6d is a sectional view of the gas regulating valve of FIG. 6a with a closed leakage orifice;

FIG. 6f is an exploded sectional view of the gas regulating valve of FIG. 6a;

FIG. 7a is a schematic representation of a gas regulating valve according to the first and second embodiments of the invention, in normal operation, during the inspiration phase;

FIG. 7b is a schematic representation of a gas regulating valve according to the first and second embodiments of the invention, in normal operation, during the expiration phase;

FIG. 7c is a schematic representation of a gas regulating valve according to the first and second embodiments of the invention, when the controller is disabled;

FIG. 8a is a schematic representation of a gas regulating valve according to the third embodiment of the invention, in normal operation, during the inspiration phase;

FIG. 8b is a schematic representation of a gas regulating valve according to the third embodiment of the invention, in normal operation, during the expiration phase.

FIG. 9b is another three-dimensional exploded view of the gas regulating valve of FIG. 9a;

FIG. 9c is a exploded plan view of the gas regulating valve of FIG. 9a;

FIG. 9d is a sectional view of the gas regulating valve of FIG. 9a with an opened leakage orifice;

FIG. 9e is a partial sectional view of the return of the gas regulating valve of FIG. 9a;

FIG. 10a is a three-dimensional exploded view of a gas regulating valve according to a fourth embodiment of the invention;

FIG. 10b is another three-dimensional exploded view of the gas regulating valve of FIG. 10a;

FIG. 10c is a exploded plan view of the gas regulating valve of FIG. 10a;

FIGS. 11a-11f are different views of all or part of a regulating valve arrangement (herein called "active valve") which can be said be incorporated in a breathing assistance device as mentioned above and illustrated in the preceding figures, but which is not limited to such device.

DETAILED DESCRIPTION

Structure

General Structure of the Device

Figure 1B:
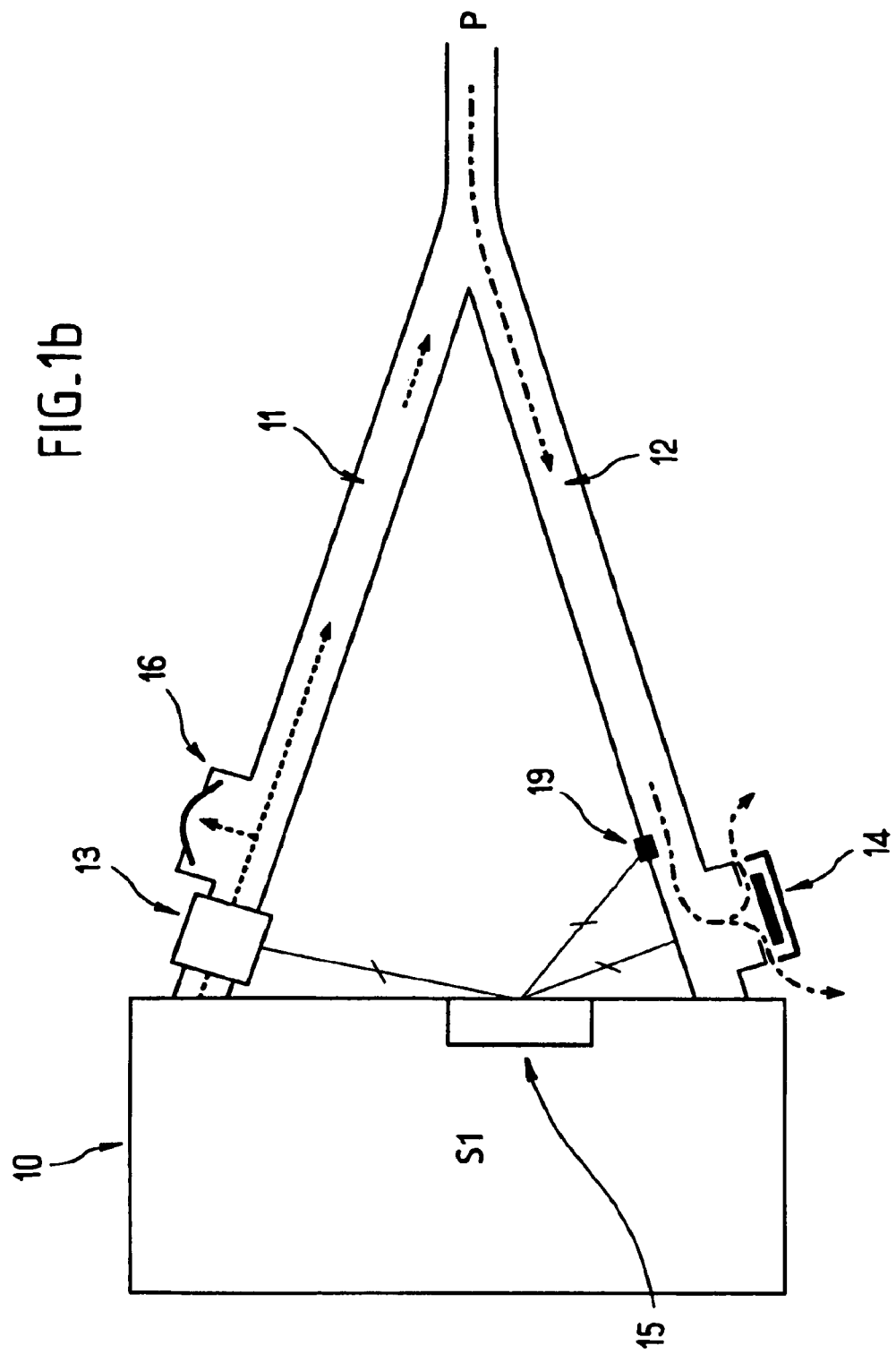
Figure 2A:
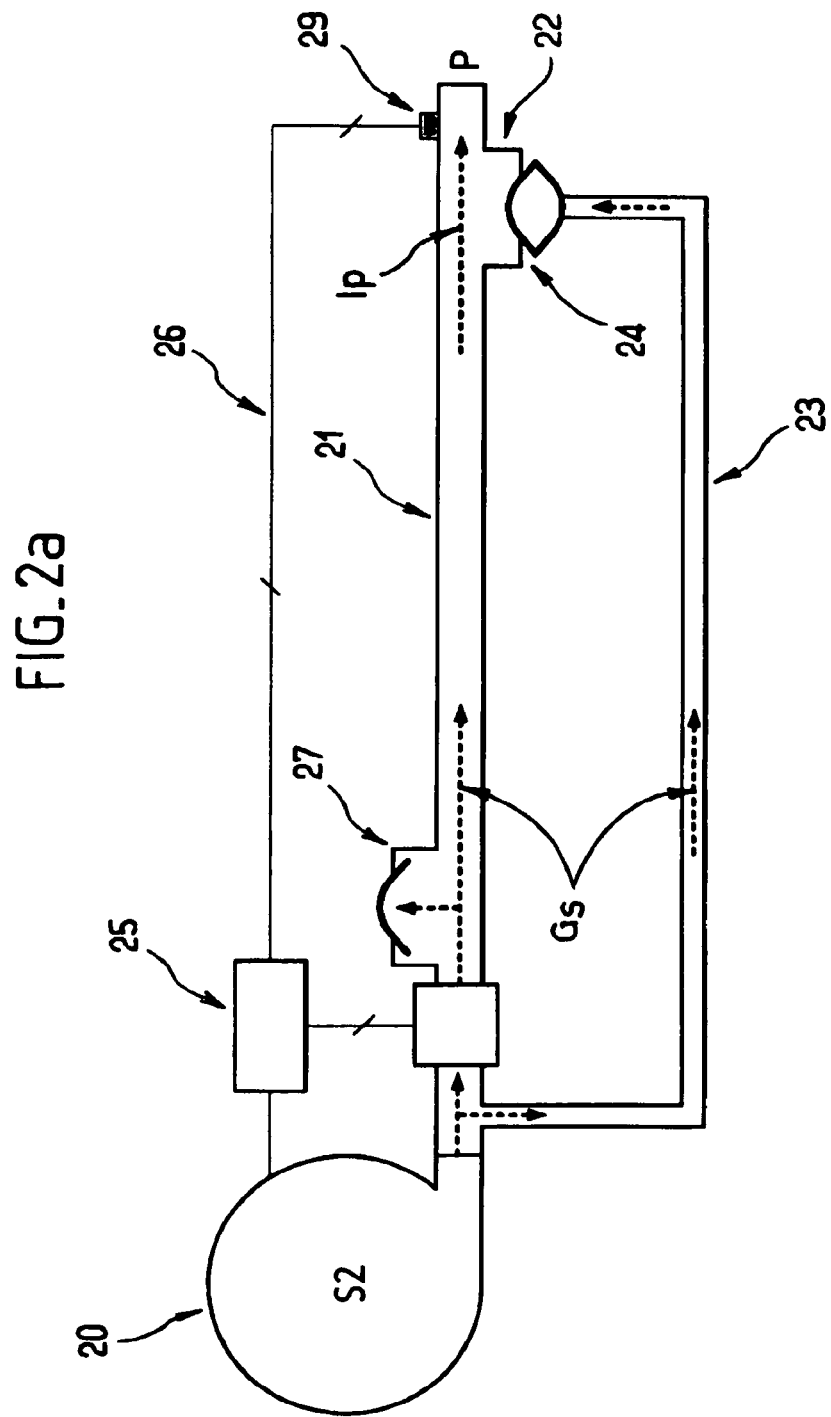
Figure 2B:
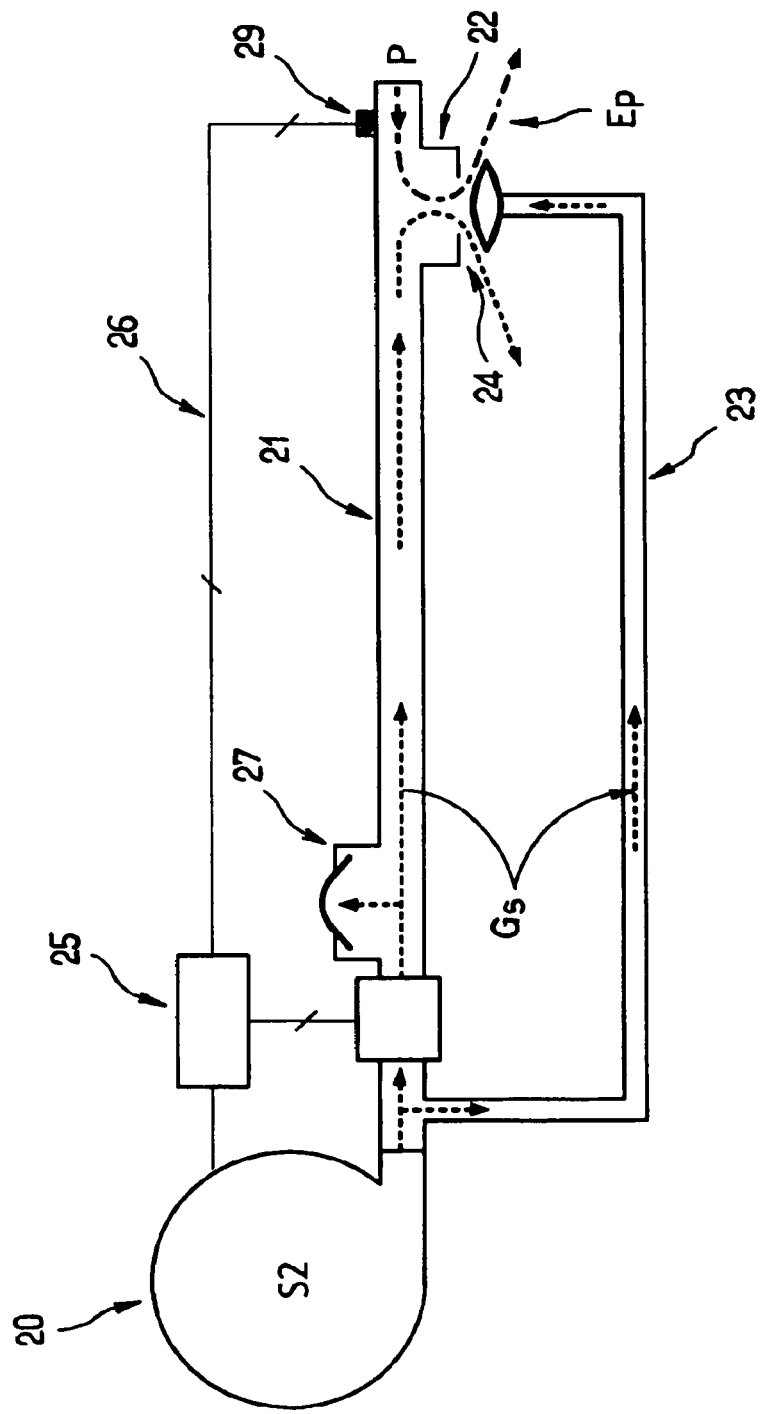

We shall first describe the general structure of a device (respirator) according to the invention. With reference to FIG. 3, a breathing assistance device according to the invention is shown in a schematic manner.

This device comprises a central unit 30, which itself includes an internal gas source S for supplying a patient P with respiratory pressurized gas. The gas source S is typically a small blower.

The breathing assistance device further comprises a gas transmission circuit between the central unit 30 and the patient P, so as to allow the patient P to inspire and expire.

A gas regulating valve 32 is interposed in said gas transmission circuit at a proximal location. By proximal location, it has to be understood that the gas regulating valve 32 is located near (i.e. typically a few centimeters) the end of the gas transmission circuit coupled to the patient P. As shall be described further in this text, the regulating valve can be made according to different embodiments (and it can furthermore comprise a specific valve arrangement described in the "active valve" section).

The gas source S will preferably be capable of operating according to several respiratory modes.

This gas source is connected to an air inlet 33a for collecting ambient air to be provided to the patient P.

An additional inlet 33b may also be provided for a secondary respiratory gas such as oxygen, in order to enrich the ambient air.

The gas source S is powered through a power supply means, i.e. a power supply 37. This power supply 37 means may be an internal battery or an external power supply.

The gas transmission circuit may be composed of one or more gas transmission ducts. As shown in FIG. 3, the breathing assistance device of the invention preferably includes a gas transmission circuit consisting of a single gas transmission duct 31.

This gas transmission duct 31 comprises a distal end 31d coupled to the source S and a proximal end 31p coupled to the patient P.

The proximal end 31p of the transmission duct 31 is connected to the patient P through a connecting means, i.e. a patient interface 36. This patient interface 36 may be e.g. a device adapted for tracheotomy or a mask.

The breathing assistance device further includes a controller 35 for controlling the gas regulating valve 32 via a connection link 39 (for data transmission and power supply). This connection link 39 can be a connection cable 39.

The controller 35 is associated to measurement means, i.e. sensors 34 (in particular a gas flow sensor and a pressure sensor).

More precisely, "associated to" means that the controller 35 either includes such sensors 34, or is connected to them via a connection link.

Part or all of these sensor(s) can indeed be located proximally, that is located near the gas regulating valve 32. It is also possible that part or all of these sensor(s) are located on the rest of the gas transmission duct 31, such as near its distal end 31d.

The controller 35 further includes data processing means, i.e. data processors, in particular to enable processing of the signals coming from the different sensor(s).

The data processors of the controller 35 are generally all located at a distal position, that is on the gas source S.

However, a data processor 38 may be located at a proximal position, that is near the patient P. Indeed, the more sensors there will be near the gas regulating valve 32, the more wires there will have to be in the connection cable 39 along the gas transmission duct 31, in order to power supply these sensors but also to collect the different emitted signals.

It is therefore interesting to provide a proximal data processor 38 so that the different signals from the sensor can be processed to be transmitted to distal data processor of the controller 35 through a single data transmission wire. Such a configuration of the data processor will therefore emphasize the miniaturization process, the connection cable 39 between the distal data processing device and the proximal sensor needing only three wires, i.e. one data transmission wire and two power supply wires.

The gas transmission duct 31 may be of different diameters. In particular, this gas transmission duct 31 may have a smaller diameter than the ducts used in the known breathing assistance devices as those represented in FIGS. 1a through 1d and 2a through 2d.

The particular gas regulating valve 32 of the invention, interposed in the gas transmission duct 31, enables namely to fulfil the pressure loss and safety standards without needing a minimal diameter duct. It is therefore possible for the gas transmission duct 31 to have a diameter smaller than 22 mm for adults and 15 mm for children.

The gas regulating valve 32 has indeed a structure that emphasizes the miniaturization of the breathing assistance device. In fact, the gas regulating valve 32 is electrically controlled no air feeding conduit is required leading thus to a more compact device. Further, as explained above, the gas transmission duct may be smaller than the usual ones. Finally, miniaturization of the breathing assistance device is increased when using a data processor located on the gas regulating valve, i.e. proximally. As exposed further in this text, the breathing assistance device remains also highly safe and reliable.

First Embodiment of the Invention

The breathing assistance device according to a first embodiment of the invention comprises a gas regulating valve as represented in FIGS. 4a to 4e. The gas regulating valve 40 according to this embodiment of the invention is mounted coaxially relative to the gas transmission duct 31.

The gas regulating valve 40 includes a casing made of three hollow portions, namely a distal portion 41, a central portion 42 and a proximal portion 43.

The three portions are coaxially connected together so as to form an integral casing. Each portion is formed so that the casing comprises a passage through which the pressurized gas can circulate form the gas source S to the patient P and vice-versa.

The distal portion 41 and proximal portion 43 are formed to be connected to the gas transmission duct 31, respectively in direction of the source S and the patient P.

The proximal portion 43 is provided with an aperture 431 so as to form a leakage orifice between the inside and the outside of the gas regulating valve 40. Gas may therefore leak from the gas transmission circuit to the atmosphere and vice-versa. It is preferred that this aperture is as wide as possible, that is the aperture covers most of the circumference of the proximal portion 43.

The gas regulating valve 40 further includes an obstruction means, i.e. an obstruction element 44 in order to vary the opening of the leakage orifice. The obstruction element 44 is preferably an electromagnetic obstruction element.

The obstruction element 44 includes a metallic toric sheath 441, preferably made of soft iron, wherein a coil 442 is fixed. This assembly is fixed around the proximal portion 43 and is surrounded by the central portion 42 of the casing.

The coil 442 may be a single toric coil but it is preferable to use two coaxial toric coils, both surrounded by the toric sheath 441. The coil 442 is powered by the controller 35 via the connection cable 39.

The obstruction element 44 further includes a magnetic element comprising a toric magnet 444, a first polar piece 443 and a second polar piece 445. The polar pieces are coaxially fixed on either side of the toric magnet 444, and are of different polarities. The polar pieces have a rotational symmetry relative to the axis of revolution of the toric magnet 444 and include a passage through which gas can circulate from the source S to the patient P and vice-versa.

This magnetic element is arranged within the proximal portion 43 and is at least partially surrounded by the coil 442. The magnetic element is movable within the proximal portion 43, it is namely translatable along the axis of revolution of the toric magnet 444. This translation movement is at least partially confined within the coil 442, the two extreme positions being defined by abutments provided in the inner side of the casing.

The magnetic element is provided with an obstruction piece 446 capable of obstructing the leakage orifice 431 of the proximal portion 43. This obstruction piece 446 is fixed on a polar piece of the magnetic element and follows therefore the translation movement of the magnetic element.

Dimension and shape of the obstruction piece 446 depend on the characteristics of the leakage orifice 431 and the magnetic element. The obstruction element 44 must namely be dimensioned so that the obstruction piece 446 totally closes the leakage orifice 431 when the magnetic element is positioned in one of its two extreme positions. The obstruction piece 446 is also preferably made of a hard material.

The magnetic element is therefore composed of different pieces, whose shapes and configuration allow a passage, through which gas can circulate form the gas source S to the patient P and vice-versa.

Another arrangement of this embodiment of the invention would be to have an obstruction element including a fixed magnetic element, that is at least a fixed magnet, and a movable coil, said movable coil being provided with an obstruction piece so as to be capable of obstructing the leakage orifice of the proximal portion. Such arrangement may take the form of the fourth embodiment described below.

Second Embodiment of the Invention

Another embodiment of a breathing assistance device according to the invention comprises a gas regulating valve as represented in FIGS. 5a to 5e. The gas regulating valve 50 of this second embodiment is very similar to the gas regulating valve 40 according to a first embodiment of the invention.

The gas regulating valve 50 of the second embodiment has namely the same structure as the gas regulating valve 40 according to a first embodiment of the invention, in particular concerning the obstruction element. However, the gas regulating valve 50 comprises a proximal portion 53 being provided with a housing 532 for sensor(s) connected to the controller 35 via the connection cable 39.

There is for example provided a gas flow pressure sensor (such as a hot wire sensor) and a pressure sensor. In this case the connection cable 39 comprises at least seven wires. There will namely be needed two power supply wires for the flow pressure sensor, two power supply wires and a data transmission wire for the pressure sensor, and two additional wires to power supply the magnetic mechanism of the gas regulating valve 50.

Third Embodiment of the Invention

A third embodiment of a breathing assistance device according to the invention comprises a gas regulating valve as represented in FIGS. 6a to 6f. The gas regulating valve 60 according to this embodiment of the invention is mounted transversally relative to the gas transmission duct 31.

The gas regulating valve 60 comprises a casing 61 having a distal end 611 and a proximal end 612, the distal end 611 being coupled to the gas transmission duct 31 in direction of the source S and the proximal end 612 being coupled to the gas transmission duct 31 in direction of the patient P.

The casing 61 has a shape very similar to a duct except the fact that it also includes a housing 613 for receiving an obstruction element 62.

A first aperture 614 is provided between the duct 616 of the casing 61 and a first zone 6131 of the housing 613.

A second aperture 615 is provided in the first zone 6131 of the housing 613, so that a gas flow may circulate between the inside of the casing 61 and the outside.

The first and second apertures (614,615) thus define a leakage orifice 617. Gas may circulate through this leakage orifice 617 from the gas transmission circuit to the atmosphere and vice-versa.

A cover 63 is foreseen to close the housing 613 and protect the obstruction element 62 disposed in a second zone 6132 of said housing 613.

The obstruction element 62 is preferably an electromagnetic obstruction element.

The obstruction element 62 comprises a metallic armature 622 which is fixed in the second zone 6132 of the housing 613. This armature 622 may be made of soft iron. The armature 622 comprises a cylindrical passage 6221 whose axis of revolution is perpendicular to the duct 616 of the casing 61.

The armature 622 is preferably a revolution solid whose axis of revolution corresponds to the axis of revolution of the cylindrical passage 6221. The armature 622 comprises a bottom disc 6222 having a circular opening at its centre and a top disc 6223 having a circular opening at its centre, the diameters of the bottom disc 6222 and of the circular opening of the bottom disc 6222 being respectively larger than the diameters of the top disc 6223 and of the circular opening of the top disc 6223.

Bottom and top discs (6222,6223) are coaxially coupled together through a peripheral coaxial cylindrical portion 6224 having the same diameter as the one of the bottom disc's circular opening.

A central coaxial cylindrical portion 6225 is provided in the armature 622, between the bottom disc 6222 and the top disc 6223. This central coaxial cylindrical portion 6225 has the same diameter as the one of the top disc's circular opening, and has an end fixed to the top disc 6223.

A central disc 6226 having the same diameter as the one of the central coaxial cylindrical portion 6225 is coaxially fixed to the other end of the central coaxial cylindrical portion 6225. This central disc 6226 is provided with a circular opening at its centre.

In this configuration, the peripheral and central coaxial cylindrical portions (6224, 6225) of the armature 622 define a toric space 6227.

The obstruction element 62 further comprises a coil 621 that surrounds the first cylindrical portion of the armature 622.

This configuration creates therefore an air-gap in the toric space 6227, between the coil 621 and the central coaxial cylindrical portion 6225 of the metallic armature 622, which is closed at one end with the top disc 6223 of the armature 622.

The obstruction element 62 also includes a magnetic element, the magnetic element comprising a toric magnet 624 and a magnet guide 623.

The magnet guide 623 is a revolution solid comprising a bottom disc 6231 and a top disc 6232 of a larger diameter, the top disc 6232 having a circular opening at its centre, the diameter of this opening being the same as the diameter of the top disc. The bottom and top discs (6231,6232) are coaxially coupled through a peripheral coaxial cylindrical portion 6233 having a diameter identical to the diameter of the bottom disc 6231. A central coaxial cylindrical portion 6234 having a smaller diameter is provided on the bottom disc 6231, between the top and bottom discs (6232,6231).

The toric magnet 624 has an inner diameter similar to the diameter of the first cylindrical portion 6233 of the magnet guide 623, so that the magnet guide 623 is inserted within the toric magnet 624.

The outer diameter of the toric magnet 624 is similar to the inner diameter of the peripheral coaxial cylindrical portion 6224 of the armature 622. The diameter of the circular opening of the top disc 6232 of the magnet guide 623 is similar to the outer diameter of the central coaxial cylindrical portion 6225 of the armature 622. The central coaxial cylindrical portion 6234 of the magnet guide 623 has an outer diameter similar to the diameter of the circular opening of the central disc 6226 of the armature 622. Therefore the magnetic element can be coaxially inserted within the toric space 6227 defined by the peripheral and central coaxial cylindrical portions (6224,6225) of the armature 622.

The magnetic element is movable, it is namely translatable along the axis of revolution of the armature 622, within the toric space 6227 defined by the peripheral and central coaxial cylindrical portions (6224,6225) of the armature 622.

An annular ridge 6141 is provided within the housing 613 on the periphery of the first aperture 614. The outer diameter of the toric magnet 624 is larger than the diameter of the first aperture 614. Therefore the translation movement of the magnetic element is confined between the armature 622 and the first aperture 614. More precisely the magnetic element abuts against the armature 622 in a first extreme position (see FIG. 6e) and against the annular ridge 6141 of the first aperture 614 in a second extreme position (see FIG. 6d).

In the second extreme position (see FIG. 6d), the magnetic element of the obstruction element 62 totally closes the first aperture 614 and thus prevents any gas flow between the duct 616 of the gas regulating valve 60 and the housing 613. As a consequence, in this second extreme position, no gas can circulate between the inside and the outside of the gas regulating valve 60.

In this configuration of the obstruction element 62, the magnetic element translates within the toric space 6227 depending on the state of the coils 621 controlled by the controller 35.

The obstruction element 62 further comprises a spring 626 having an outer diameter similar to the inner diameter of the central coaxial cylindrical portion 6225 of the armature 622, and which is inserted within said central coaxial cylindrical portion 6225 of the armature 622. The spring 626 is preferably a compression spring.

The spring 626 is maintained within the central coaxial cylindrical portion 6225 of the armature 622 with a screw 627 which is screwed within the central coaxial cylindrical portion 6225 of the magnet guide 623. The spring 626 has namely an end abutting against the head of the screw 627 and another end abutting against the central disc 6226 of the armature 622.

The gas regulating valve 60 may comprise a protection element 625 within the housing 613 of the casing 61. This protection element 625 delimits the first and second zones within the housing 613, the first zone 6131 wherein the first and second apertures (614,615) are located and the second zone 6132 containing the obstruction element 62.

The protection element 625 is gas impermeable and prevents therefore gas within the duct of the gas regulating valve 61 from polluting the obstruction element 62.

The protection element 625 may be a rubber membrane. This membrane is a revolution solid comprising a central disc 6251, this central disc 6251 having a relatively large peripheral and circular groove 6252.

The peripheral edge of the protection element 625 is pressed by the armature 622 against a circular abutment between the first and the second zone of the housing 613. The annular ridge 6228 of the armature 622 prevents the peripheral edge of the protection means 625 from moving.

Another arrangement of this embodiment of the invention resides in an obstruction element comprising a magnetic element being fixed, that is at least a magnet being fixed, and a movable coil, said movable coil allowing the obstruction of the leakage orifice.

The housing 613 may comprise a third zone 6133 for receiving sensor(s) 65 such as gas flow and/or pressure sensors for measuring gas flow and/or pressure in the duct of the gas regulating valve 60.

The sensor(s) 65 may be directly connected to the controller 35 located on the source S, via the connection cable 26. In this case, the connection cable 39 is provided with a least seven wires (two power supply wires for the flow pressure sensor, two power supply wires and a data transmission wire for the pressure sensor, and two additional wires to power supply the magnetic mechanism of the gas regulating valve).

Therefore, a processing means 64 is preferably provided between the sensor(s) 65 and the connection cable 39. This processing means 64 is located within the housing 613 and lies on both the sensor(s) 65 and the obstruction element 62.

The processing means 64 is connected to both the sensor(s) 65 and the obstruction element 62. Thus the processing means 64 allows the sensor(s) 65 and the obstruction element 62 to be power supplied. Moreover the processing means 64 is capable of managing the data from the sensor(s) 65 in order to precisely control the obstruction element 62. The processing means 64 is capable of controlling the PEP, in processing the data from the sensor(s) 65 and operating the obstruction element 62 in consequence.

The connection cable 39 between the processing means 64 and the controller 35 is also much simpler, being provided only with three wires, i.e. two power supply wires and one data wire.

The control of the gas regulating valve 60 being totally operated by the processing means 64, the controller 35 located in the central unit 30 may also be simplified, if not totally removed. This thus contributes to the miniaturization of the breathing assistance device.

Fourth Embodiment of the Invention

A fourth embodiment of a breathing assistance device according to the invention shall now be described.

In this embodiment, the regulating valve is—like in all other embodiments—in a proximal location near the patient.

In addition to the advantages already exposed about the invention, this embodiment allows in particular:
- offering particular high performance for avoiding leakage of gas (e.g. between internal walls of inner elements of the valve), while at the same time allowing a coaxial configuration, where the main elements of the valve are aligned around the longitudinal axis of the duct (this type of configuration tends to decrease the size of the valve and hence increase capacity),
- allowing excellent performance in terms of control of the valve—in particular real-time control—since in the specific configuration of such valve the moving parts have less inertia and their quick and accurate displacement is facilitated,
- furthermore allowing smooth operation of the valve with the use of an elastic membrane having among its functions a function of smoothly restoring a reference position of the moving parts of the valve.

This fourth embodiment comprises a gas regulating valve as represented in FIGS. 9a to 9e. The gas regulating valve according to this embodiment of the invention is mounted coaxially relative to the gas transmission duct 31. According to this embodiment of the invention the obstruction element includes a fixed magnetic element with a fixed magnet, and a movable coil, said movable coil being provided with an obstruction piece so as to be capable of obstructing a leakage orifice provided in a proximal portion of the expiratory valve.

Figure 9A:
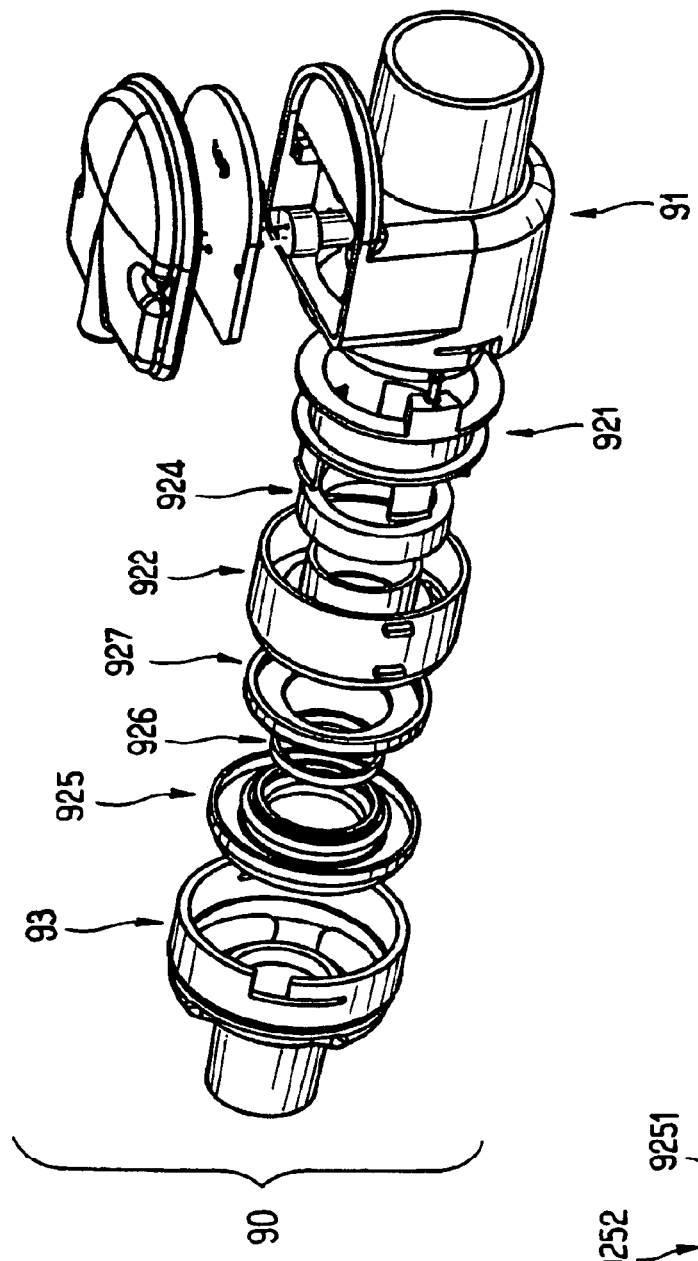
FIG. 9a is a three-dimensional exploded view of a gas regulating valve according to a fourth embodiment of the invention.
Figure 9E:
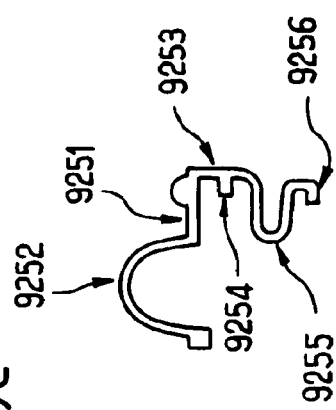
Figure 9C:
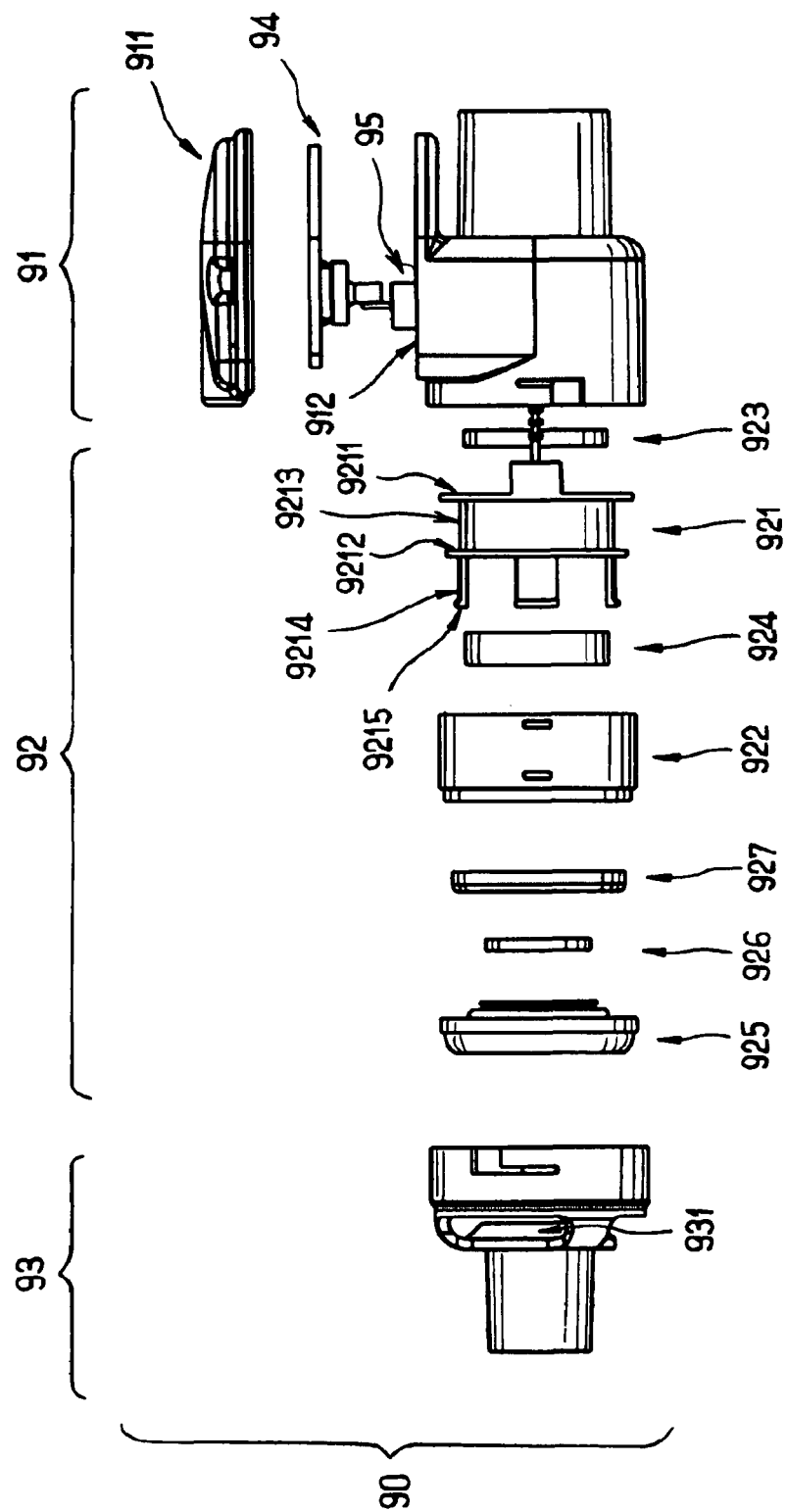

The gas regulating valve 90 includes a casing made of two hollow portions, namely a distal portion 91, and a proximal portion 93 (as illustrated in particular on FIG. 9c).

These two portions are coaxially connected together so as to form an integral casing. Each portion is formed so that the casing comprises a passage through which the pressurized gas can circulate form the gas source S to the patient P and vice-versa.

The distal portion 91 and proximal portion 93 are formed to be connected to the gas transmission duct 31, respectively in direction of the source S and the patient P.

The proximal portion 93 is provided with an aperture 931 so as to form a leakage orifice between the inside and the outside of the gas regulating valve 90. Gas may therefore leak from the gas transmission circuit to the atmosphere and vice-versa. It is preferred that this aperture is as wide as possible, that is the aperture covers most of the circumference of the proximal portion 93.

The gas regulating valve 90 further includes an obstruction element 92 in order to vary the opening of the leakage orifice. The obstruction element 92 is preferably an electromagnetic obstruction element.

In the example illustrated in FIG. 9, the obstruction element 92 comprises a metallic armature 922 which is fixed coaxially within the distal portion 91. This armature 922 may be made of soft iron.

The armature 922 is preferably a revolution solid whose axis of revolution corresponds to the axis of revolution of both proximal 93 and distal 91 portions. The armature 922 comprises two coaxial cylindrical portions, namely an inner cylindrical portion 9221 having a smaller diameter than an outer cylindrical portion 9222.

These two cylindrical portions 9221 and 9222 are coupled together with an annular portion 9223 located on the proximal side of the armature. The annular portion 9223 is provided with a plurality of apertures, each aperture having preferably the form of a curved slot.

The proximal end of the outer cylindrical portion 9222 may be provided with an annular ridge 9224 for maintaining the obstruction piece (925,926,927) of the obstruction element 92 (described below) pressed between the armature 922 and the proximal portion 93.

The obstruction element 92 further includes a magnetic element comprising a toric magnet 924 and a toric metallic piece 923.

Both the toric magnet 924 and the toric metallic piece 923 have an inner diameter similar to the outer diameter of the inner cylindrical portion 9221. The toric magnet 924 and the toric metallic piece 923 both surround the inner cylindrical portion 9221 of the armature 922, in a fixed manner.

The outer diameter of the toric magnet 924 and the toric metallic piece 923 is smaller than the inner diameter of the outer cylindrical portion 9222, thus creating a toric space 9225 within the armature 922. There is therefore an air-gap within the toric space 9225, between the toric magnet 924 and the outer cylindrical portion 9222 of the metallic armature 922, which is closed at one end with the annular portion 9223 of the armature 922.

The obstruction element 92 further includes a movable coil 921 adapted to be inserted within the toric space 9225, and to be coaxially translatable therein.

The movable coil 921 is preferably a revolution solid whose axis of revolution corresponds to the axis of revolution of the armature 922. The movable coil 921 comprises a bottom disc 9211 having a circular opening at its centre and a top disc 9212 having a circular opening at its centre. The diameters of the circular opening of the bottom 9211 and top 9212 discs are both similar to the outer diameter of the toric magnet 924. The outer diameter of the top disc 9212 is similar to the inner diameter of the outer cylindrical portion 9222 of the armature 922, so that the top disc 9212 can translate within the toric space 9225. The outer diameter of the bottom disc 9211 is larger than the inner diameter of the outer cylindrical portion 9222 of the armature 922, so that the bottom disc 9212 may abut against the armature 922 to limit the translation movement of the coil 921.

Bottom 9211 and top 9212 discs are coaxially coupled together through a coaxial cylindrical portion 9213 having the same diameter as the circular openings of the discs.

Top disc 9212 is provided with a plurality of projecting portions 9214 around its circular opening. Each projecting portion 9214 is substantially flat and curved with the same curvature as the cylindrical portion 9213 so as to lengthen this latter. Further, each projecting portion 9214 is provided with a ridge 9215 at its proximal end, this ridge 9215 enabling coupling of the movable coil 921 with the obstruction piece (925,926,927).

The obstruction piece comprises an elastic membrane 925 (made of rubber or silicone for example) and a pusher element 927 that is adapted for deforming the membrane 925 depending on the translation of the coil 921 within the toric space 9225.

The membrane 925 is relatively resilient and is adapted to obstruct the leakage orifice 931 of the proximal portion 93 when the coil 921 is translated towards the proximal portion. The membrane 925 may be a revolution solid comprising an annular portion 9251, this annular portion 9251 having a relatively large peripheral and circular groove 9252, which is oriented proximally. The peripheral edge of the annular portion 9251 is maintained pressed between the proximal portion 93 and the outer cylindrical portion 9222 of the armature 922.

The membrane 925 is further provided with a cylindrical portion 9253 having a similar diameter to the inner diameter of the annular portion 9251. This cylindrical portion 9253 is provided with an annular ridge 9254 for coupling the pusher element 927 to the membrane 925.

Finally the membrane 925 comprises a bellows 9255 extending from the cylindrical portion 9253 and comprising an annular ridge 9256 (not visible in FIG. 9e). This annular ridge 9256 enables the inner edge of the membrane 925 to be maintained on the armature 922 with a toric element 926 for example.

Using such a rubber membrane 925 allows absorption of the shocks that the gas regulating valve may undergo while the obstruction piece is moving.

Further, the particular form of the membrane 925, and in particular of the bellows 9255, in addition to its resilience, implies that the membrane 925 works as a return means, i.e. a return, for the coil 921. In particular, as will be explained in detail below, the membrane 925 will prevent the leakage orifice 931 to be obstructed in case operation of the coil 921 is not working correctly.

Such a membrane could also be used for other embodiments, such as a transversally mounted gas regulating valve similar to the third embodiment. Indeed, this specific membrane could be used as a return instead of the spring.

As described above, the pusher element 927 is adapted for deforming the membrane 925 on translation of the coil 921. Preferably, the pusher element 927 comprises an annular flat portion 9271 with a curved peripheral edge 9272. The curved peripheral edge 9272 is adapted to cooperate with the ridges 9215 of the projecting portions 9214 of the coil 921 so that the pusher element 927 is engaged with the coil 921. The annular flat portion 9271 is adapted to cooperate with the annular portion 9251 of the membrane 925. More precisely it enables deformation of the membrane 925, and particularly of the groove 9252 and of the bellows 9255, upon movement of the coil 921 within the toric space 9225.

This particular embodiment of the valve, and in particular the arrangement of the obstruction element within the valve, increases its reliability. Indeed, the movable coil is confined within a dedicated space which is separated from the passage of the valve through which pressurized gas circulates from the source to the patient. Therefore, this arrangement prevents undesired leakages which might happen between the movable element and the inner wall of the passage if the movable element were located inside the passage.

The gas regulating valve may further be adapted for receiving sensor(s) 95 such as gas flow and/or pressure sensors for measuring gas flow and/or pressure in the duct of the gas regulating valve 90.

To this end the distal portion 91 is provided with an external chamber 912 provided with apertures through which the sensor(s) 95 may be plugged. The active portion of the sensor is thus located within the gas duct of the valve.

The sensor(s) 95 may then be directly connected to the controller 35 located on the source S. However, similarly to the third embodiment, a processing means 94 is preferably provided between the sensor(s) 95 and the connection cable 39.

To this end, the distal portion 91 is further designed to receive the processing means 94. In this case the distal portion 91 will need to be larger to be able to receive the processing means 94. A cover 911 is in this case foreseen to close the distal portion 91 and protect both the sensor(s) 95 and the processing means 94.

Fifth Embodiment of the Invention

A variant of the invention shall now be described, in particular as an evolution of the valve described above in reference to FIG. 9.

This variant is presented as a separate—and thus fifth—embodiment of the invention since it implies a particular configuration of the valve assembly as a modular assembly made of distinct modules.

Figure 10D:
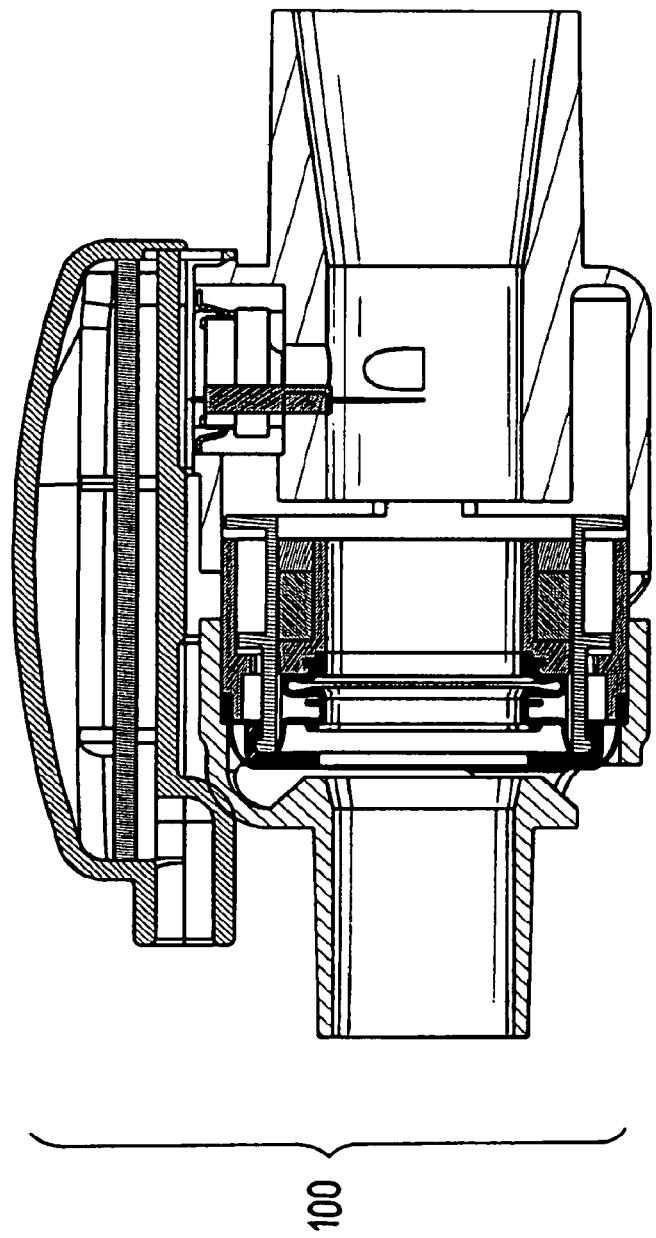
FIG. 10d is a sectional view of the gas regulating valve of FIG. 10a with an opened leakage orifice.

This modular configuration can also be used with a valve different from the valve more specifically illustrated in FIG. 10, and this configuration provides by itself a number of specific advantages which shall be mentioned in the present section.

For providing the gas regulating valve 90 with a processing means such as means 94 of FIG. 9 it is indeed possible to use an independent processing module 104, as illustrated more specifically in FIG. 10c.

FIGS. 10a to 10d represent a gas regulating valve 100 according to a fifth embodiment of the invention, this valve having an obstruction element similar to the obstruction element of the expiratory valve 90 but which is enclosed in a modular casing.

Similarly to the fourth embodiment, the gas regulating valve 100 includes a casing made of two hollow portions, namely a distal portion 101, and a proximal portion 103.

Again, these two portions are coaxially connected together so as to form an integral casing. Each portion is formed so that the casing comprises a passage through which the pressurized gas can circulate form the gas source S to the patient P and vice-versa.

However, contrary to the fourth embodiment, the distal portion 101 is more compact. Indeed, the distal portion 101 is designed to receive only the obstruction element 102. If the sensor 105 may be plugged on the distal portion 101, there is no space provided for receiving connections to the controller 35, or any processing means. Therefore, if no measurement is needed, the gas regulating valve remains very compact and reliable.

In case measurements of the gas flow and/or pressure in the duct of the gas regulating valve are needed, an independent processing module 104 may be connected to the valve. This processing module is designed to be removably connected on the casing, that is the processing module is an independent module that may be mounted directly and easily on the casing if measurements are needed. The processing module may for example be designed to be clipped on the distal portion 101 for example.

The processing module 104 may comprise a support means 1041 provided with clipping means 1042 designed for surrounding the distal portion 101 and maintained the processing module engaged around the distal portion 101. The support means 1041 is further adapted for supporting a processing means 1044 thereon. An aperture 1043 through the support means 1041 is also foreseen so that the processing means 1044 may be connected to the sensor 105 plugged on the distal portion 101.

Finally, a cover 1045 encloses the processing means 1044 on the support means 1041 to protect it. An aperture is also provided through the cover 1045 to connect the processing means 1044 to the controller 35.

Not only this gas regulating valve has the advantage of being compact, the modular arrangement is also very advantageous in terms of maintenance.

The valve being intended to be used mostly for medical applications, the valve must be adapted for sterilization processes, with an autoclave for example. More precisely, each element that may have been polluted by the gas flow must be adapted for sterilization. This is the case of the distal portion 101, the obstruction element 102, the proximal portion 103, and eventually the sensor 105. Indeed, the processing module 104 is completely independent from the gas flow passage which means that it does not need to be autoclaved contrary to the other elements. This is particularly advantageous as it would be particularly difficult and expensive to manufacture an autoclavable processing module 104, and more particularly an autoclavable processing means 1044. It would namely be expensive to have a processing means 1044 with autoclavable components. Further, the connections and particularly the connection between the processing means 1044 and the controller 35 may not withstand an autoclave curing.

A further advantage of having an independent processing module is that it may be removed from the valve as a single unit, thus preventing any damages of the processing module 1044 or of the connections.

Sixth Embodiment of the Invention

In reference now to FIGS. 11a to 11f, a valve arrangement which can be used in accordance with the invention shall now be described.

This valve arrangement can in particular be used in a regulating valve in a breathing assistance device as mentioned above and generally illustrated in FIG. 3.

However such valve arrangement constitutes in itself a specific feature which can be used in different valve and/or device configurations.

An example of a very compact breathing assistance device 110 is illustrated in FIG. 11f, with:
- a blower 111 (in fact a compressor blower, but generally called a "blower") for feeding a patient with compressed air (the blower being possibly provided with an inlet for a secondary gas such as oxygen),
- a valve housing 112, sealingly attached to the outlet 1110 of the blower by its first end 1121,
- a valve 113, arranged into the valve housing and having an outlet 1131 which can be directly put in contact with the patient (i.e. the patient breathes directly at outlet 1131).

Figure 11A:
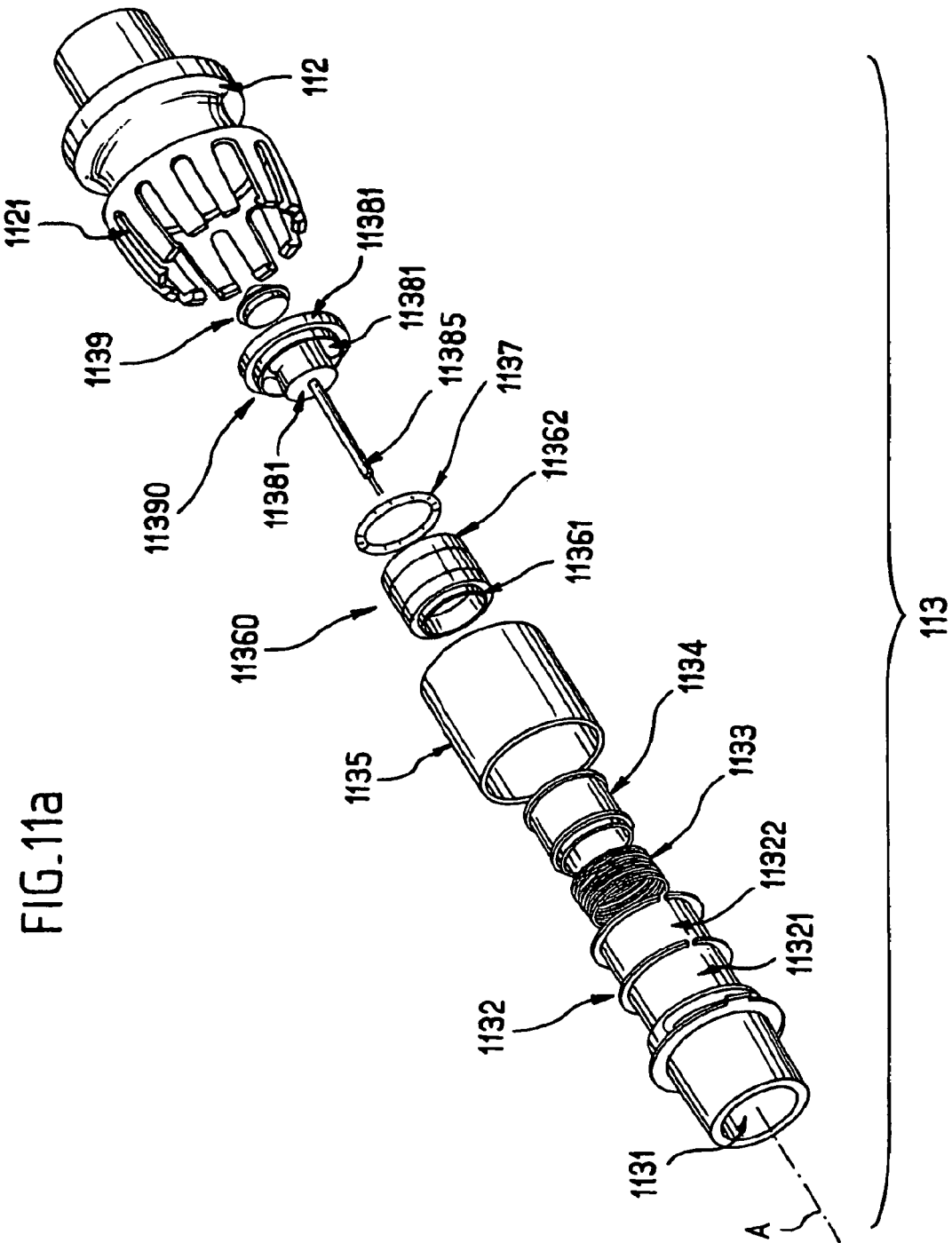

FIG. 11a illustrates in an exploded view the elements of the valve 113.

These elements are arranged coaxially, aligned around the axis A of the valve housing 112 (which is typically itself aligned with the outlet of the blower).

On the exploded view of FIG. 11a, these elements are, from the proximal end of the valve (side opposed to the valve housing) to its distal end (side close to the valve housing):

the outlet 1131 which is on a hollow valve body 1132,
the valve body 1132 has two stages of coil 11321 and 11322 aligned in sequence along the axis A
a spring 1133,
a cylinder 1134, made of a material such a plastic, adapted to be light (since this cylinder has to be easily moved), adapted to be engaged in the central cavity of the valve body,
another cylinder 1135 in a material such as iron, and having an inner diameter corresponding to the outer diameter of the valve body 1132 with its coils,
an assembly 1136 made of a permanent magnet 11360 axially surrounded by two iron cylinders 11361 and 11362, all three items forming a single assembly 1136 made of one piece. This assembly is hollow and has the general shape of a ring since all its components have a central axial hole,
an O-ring 1137,
a ring 1138 called a flow-path ring, since it is provided with holes 13380 disposed regularly around its central axis, for letting the flow of gas circulate through, (these holes 11380 are separated by radial arms which join a central part of the flow-path ring 11381 to its periphery 11382—these arms are not visible on the figure). The number of holes can be adapted (e.g. two, three, or more holes disposed regularly around the periphery of the central part—or even a single hole),
the outer diameter of the central part of the flow-path ring corresponds to the inner diameter of the assembly, with a tolerance allowing relative movement of these two elements along the axis A,
and the distal end of the assembly 1136 has a width which is adapted to close the holes 11380 of this flow-path ring,
more precisely, once the elements are mounted together, the flow-path ring 1138 is sealingly mounted inside the distal end of the valve body, so as to define an inner channel 11350 having the shape of a ring in regard of the holes 11380, said channel being between the inner wall of the valve body and the outer wall of the central part of the flow path ring (see FIG. 11b),
and the width of the assembly 1136 is the same as the width of the channel 11350, with a tolerance to allow longitudinal sliding of said assembly into this channel,
a sensor 11385 for sensing flow and/or pressure, e.g. a hot-wire sensor. This sensor is disposed on an axial arm attached to the proximal end of the central part 11381 of the flow-path ring, so as to be placed on the axis A when the device is mounted.

FIG. 11b shows that these elements form two main parts once they are mounted together:
a fixed part comprising:
the valve body with its coils,
said coils being surrounded by the iron cylinder 1135,
the flow path ring 1138 with its arm and sensor 11381, said flow path ring being mounted at the distal end of the valve body so that when said valve body is mounted inside the valve housing 112, any air coming from and going to the blower has to flow through the holes 11380,
said flow path ring 1138 being furthermore provided with a distal deflector for smoothly deflecting the air from the blower towards the holes 11380,
and a moving part comprising the following elements attached together:
the assembly 1136 (adapted as mentioned above to axially slide inside the channel 11350 so as to sealingly close this channel),
the cylinder 1134,
the spring 1133
said spring being is designed to abut against an inner shoulder 11323 of the valve body so as to push the moving part towards the distal end of the fixed part when said spring is compressed because the moving part has been displaced towards the proximal end of said fixed part.

Operation of the Device

The breathing assistance device according to the invention is capable of being operated even if the gas source S and/or the controller 35 are disabled (e.g. in case of a breakdown).

We shall describe the operation of the breathing assistance device in different cases, as illustrated in FIGS. 7a to 7c and FIGS. 8a to 8b.

Normal Operation

The normal operation of the device corresponds to the case when both the gas sources S and the controller 35 operate normally.

During the inspiration phase, the obstruction element (72; 82) of the gas regulating valve is an extreme position so that the leakage orifice (71;81) of the gas regulating valve is totally obstructed, as illustrated in FIGS. 7a and 8a.

As a consequence, when the patient P inspires, the pressurized gas $G_S$ coming from the gas source S is transmitted to the patient P. The leakage orifice (71;81) of the gas regulating valve being namely closed, the pressurized gas $G_S$ can circulate in the gas transmission duct until the patient P.

Figure 4A:
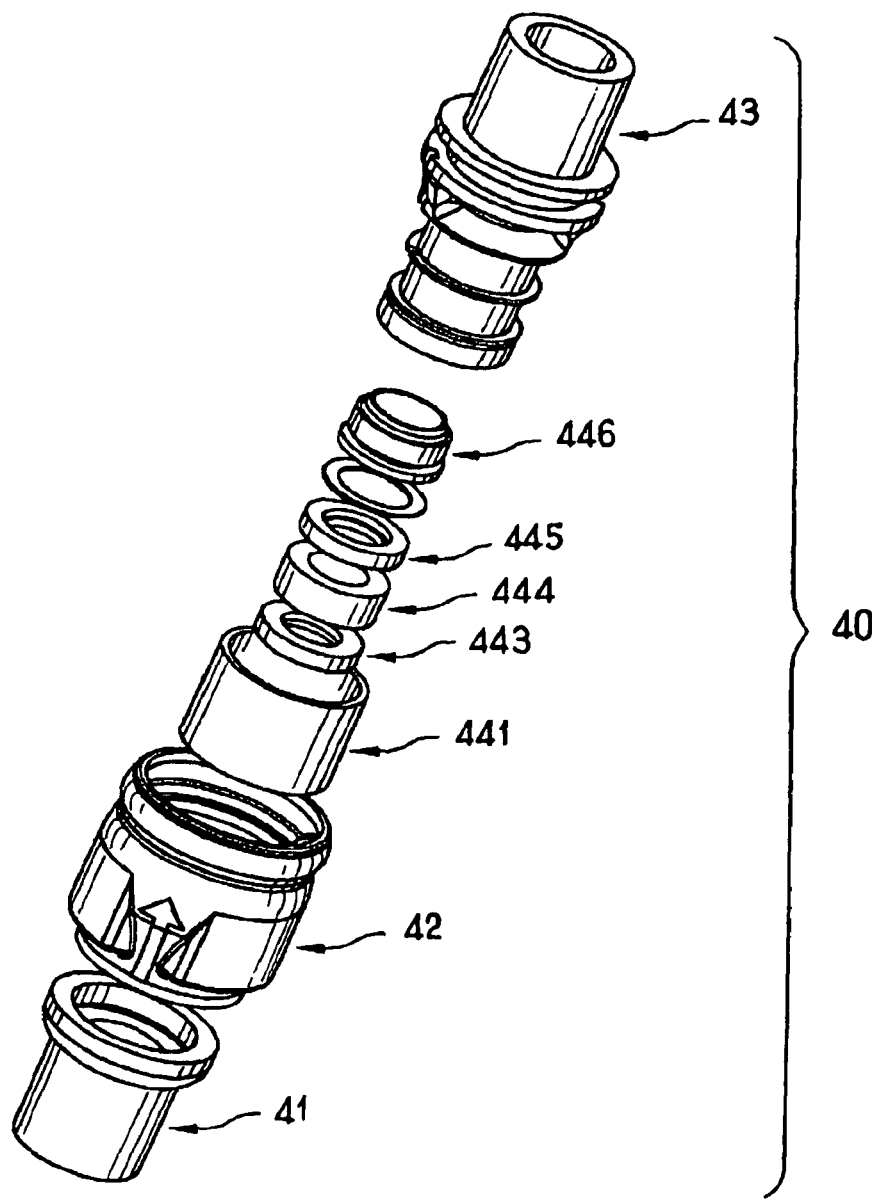
FIG. 4a is a three-dimensional exploded view of a gas regulating valve according to a first embodiment of the invention.
Figure 4D:
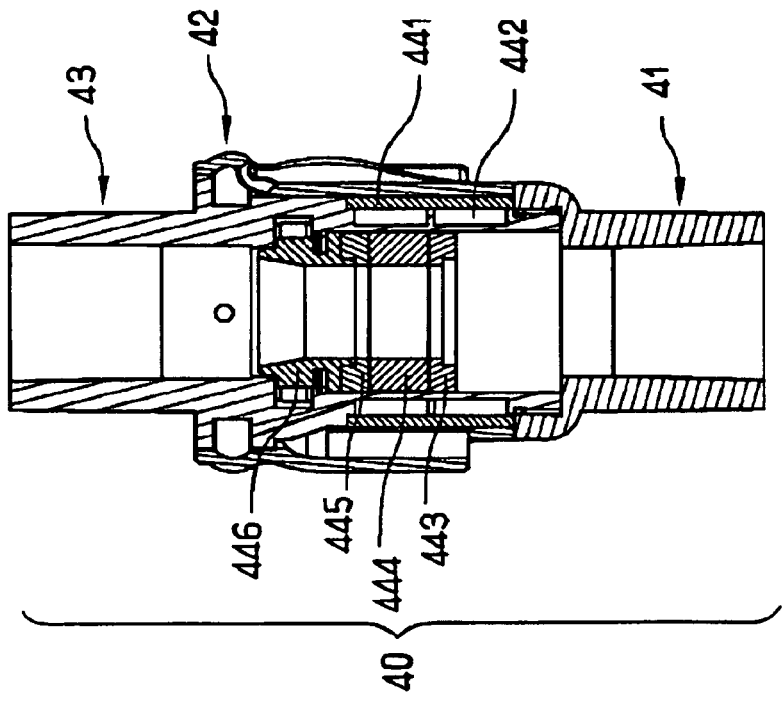
FIG. 4d is a sectional view of the gas regulating valve of FIG. 4a with a closed leakage orifice.
Figure 4C:
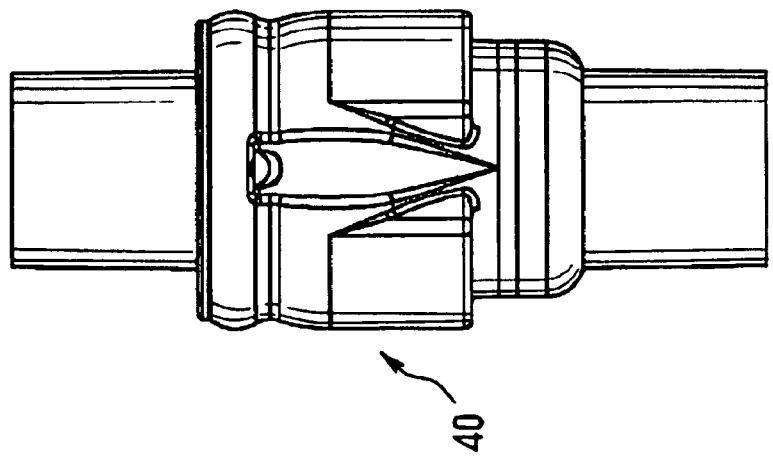

FIGS. 4d and 5d represent the gas regulating valve (40;50) according to the first and second embodiments of the invention during the inspiration phase, that is when the leakage orifice (431;531) is totally closed.

In this case, the controller 35 operates the coil (442;542) of the obstruction element (44;54) so that the magnetic element translates within the proximal portion (43;53) of the gas regulating valve (40;50) and abuts against an abutment provided within the proximal portion (43;53) of the gas regulating valve (40;50).

Therefore the obstruction piece (446;546) of the magnetic element totally closes the leakage orifice (431;531). The passage between the inside and the outside of a gas regulating valve (40;50) is thus closed and the pressurized gas coming from the gas source S only circulates from the distal portion (41;51) to the proximal portion (43;53) and then to the patient P.

Operation of the gas regulating valve according to the fourth and fifth embodiments is similar. The difference resides in the location of the obstruction element and particularly of the movable element which moves in a separate space.

FIG. 6d illustrates the gas regulating valve 60 according to the third embodiment of the invention during the inspiration phase, that is when the leakage orifice 617 is totally closed.

In this case the controller 35 operates the coil 621 of the obstruction element 62 so that the magnetic element translates until it abuts against the annular ridge 6141 of the housing 613.

Therefore the leakage orifice 617 is closed and no gas can circulate between the inside and the outside of the gas regulating valve 60. The magnetic element namely obstructs the passage provided through the first aperture 614 of the housing 613. In this situation, the pressurized gas $G_S$ coming from the gas source S has no other way but to reach the patient P.

During the expiration phase as illustrated in FIGS. 7*b* and 8*b*, the leakage orifice (71;81) is at least partially opened. The obstruction element (72;82) has namely a position so that the gas flow can circulate between the inside and the outside of the gas regulating valve through the leakage orifice (71;81).

In this case, the patient P rejects expiratory gases $E_P$ that have to be evacuated. The leakage orifice (71;81) of the gas regulating valve allows such an evacuation of the expiratory gases.

Controlling the opening of the leakage orifice (71;81) with the obstruction element (72;82) of the gas regulating valve is also a way of controlling the PEP. The PEP in the gas transmission duct is namely important for the patient P to expire correctly, as the PEP is a way to balance the residual overpressure in the patient lungs.

The obstruction element being electrically controlled, the control of the opening of the leakage orifice is a real time process.

Figure 5B:
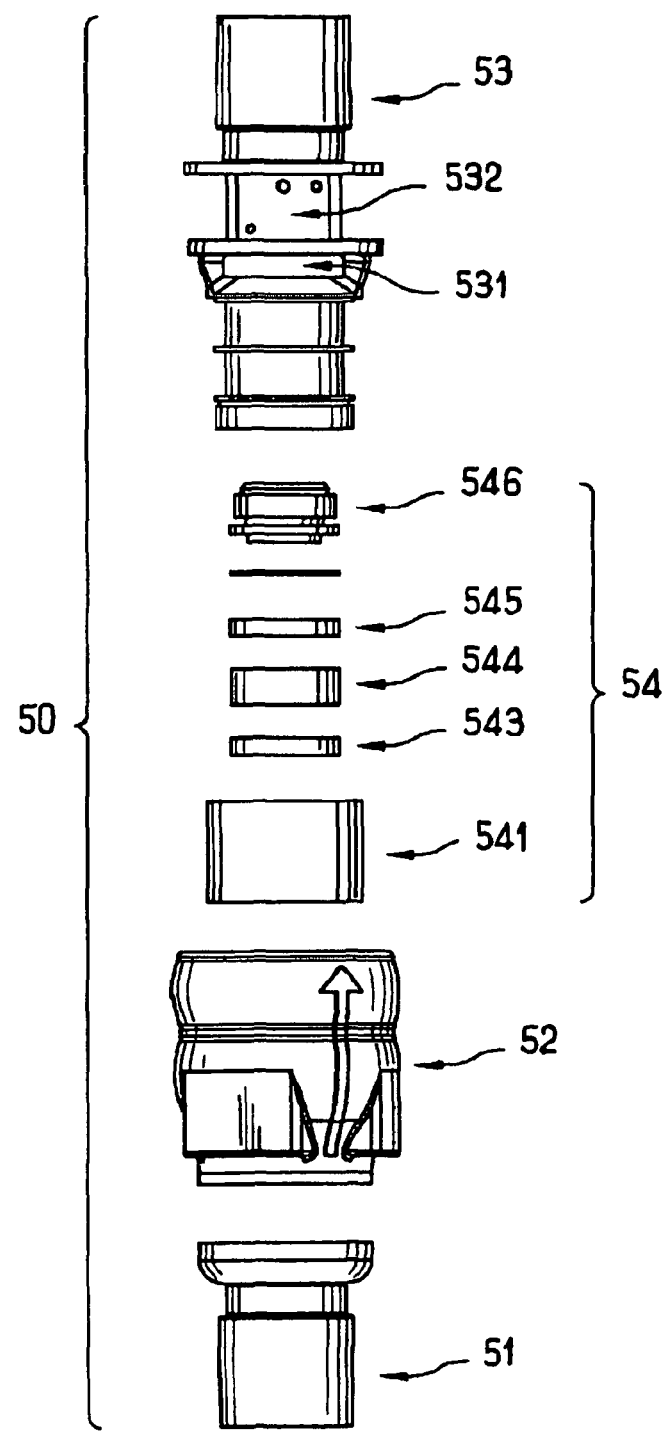
Figure 5E:
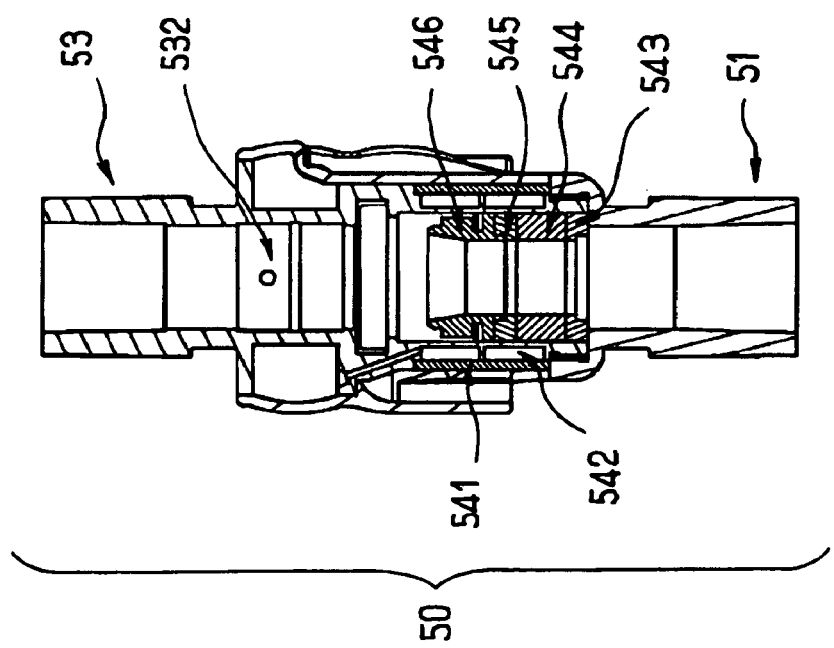
FIG. 5e is a sectional view of the gas regulating valve of FIG. 5a with an opened leakage orifice.

FIGS. 4*e* and 5*e* illustrate the gas expiratory valve (40;50) according to the first and second embodiments of the invention, during the expiration phase.

These figures namely show gas regulating valves having a leakage orifice (431;531) totally opened. The obstruction element (44;54) has indeed been operated by the controller 35 through the coil (442;542) so as to translate until an abutment provided on the distal portion (41;51) of the gas regulating valve (40;50).

Operation of the gas regulating valve according to the fourth and fifth embodiments is similar.

Figure 6E:
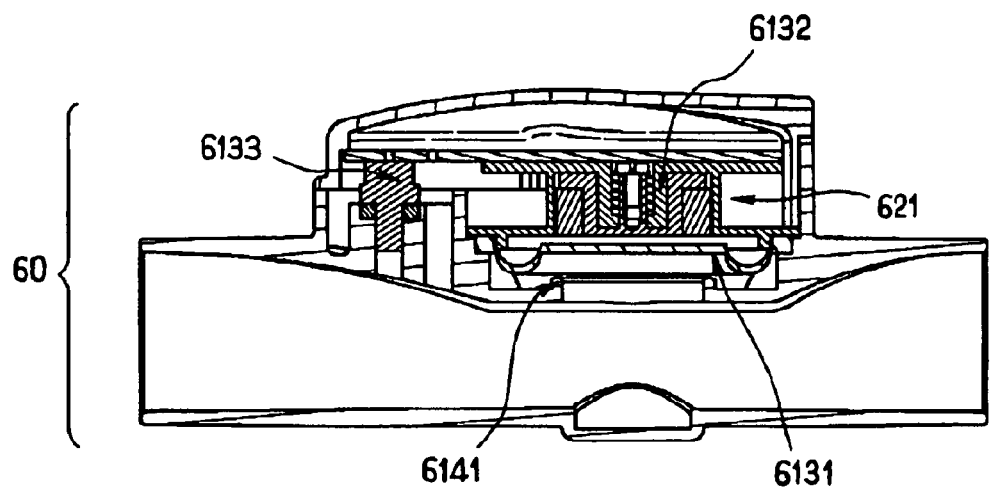
FIG. 6e is a sectional view of the gas regulating valve of FIG. 6a with an opened leakage orifice.
Figure 6C:
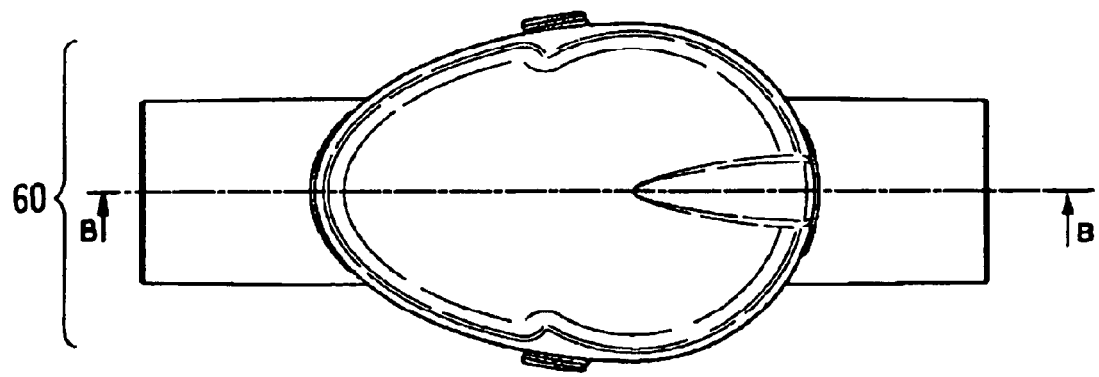

FIG. 6*e* illustrates a gas regulating valve 60 according to the third embodiment of the invention during the expiration phase.

This figure namely shows a leakage orifice being totally opened. In fact, the magnetic element of the obstruction element 62 has been operated by the controller 35 through the coil 621 in order to translate until abutting against the armature 622.

In this position, the first aperture 614 between the duct 616 and the housing 613 of the gas regulating valve is wildly opened. A gas flow can therefore circulate between the duct 616 of the gas regulating valve 60 and the housing 613, this gas flow being then able to circulate from the first zone of the housing 613 to the outside of the gas regulating valve 60 through the leakage orifice 617.

It is to be noticed that the opening of the first aperture 614 between the duct 616 and the housing 613 of the gas regulating valve 60 can be precisely controlled in translating the magnetic element of the obstruction element 62.

Figure 11C:
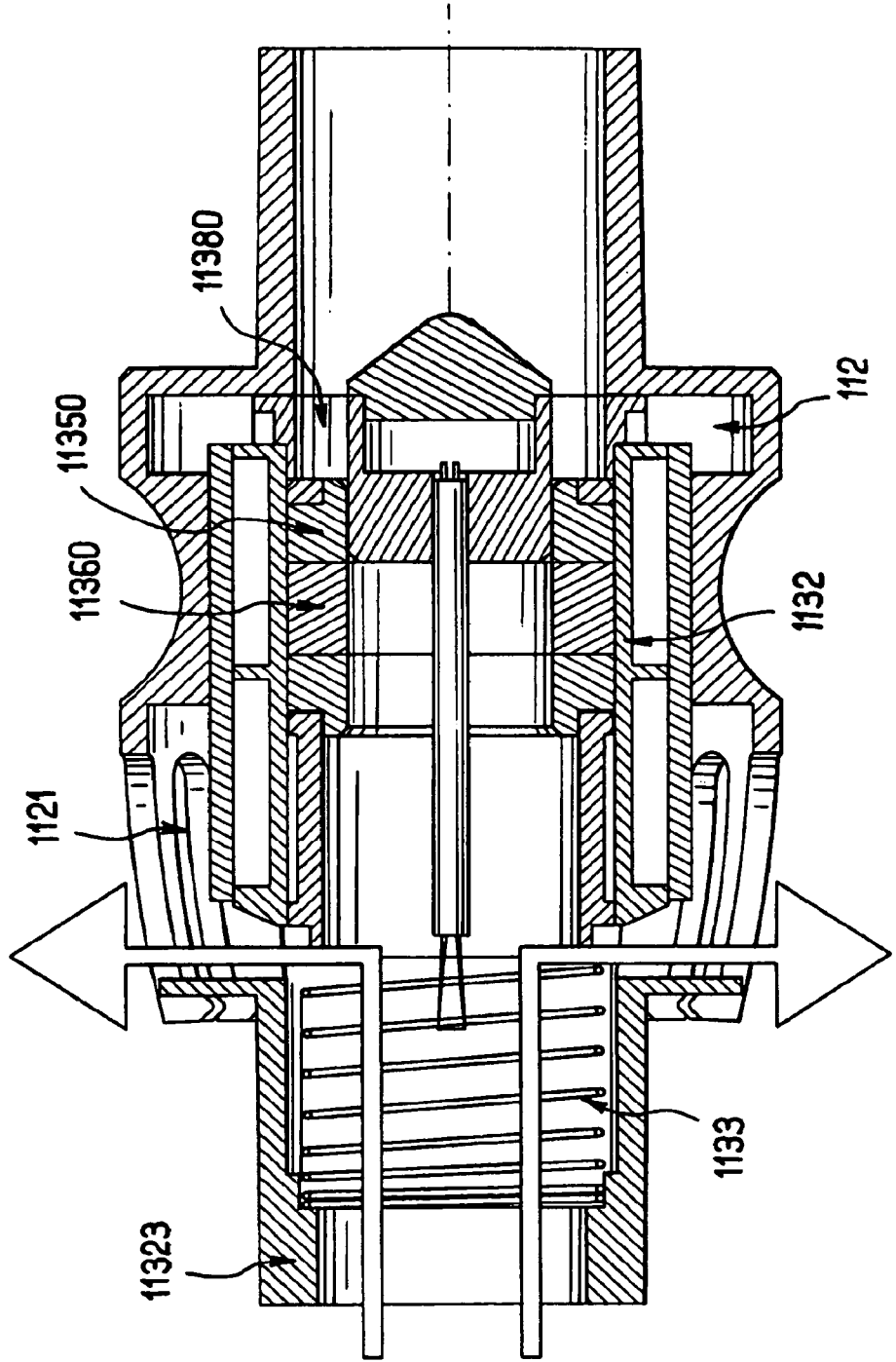
Figure 11D:
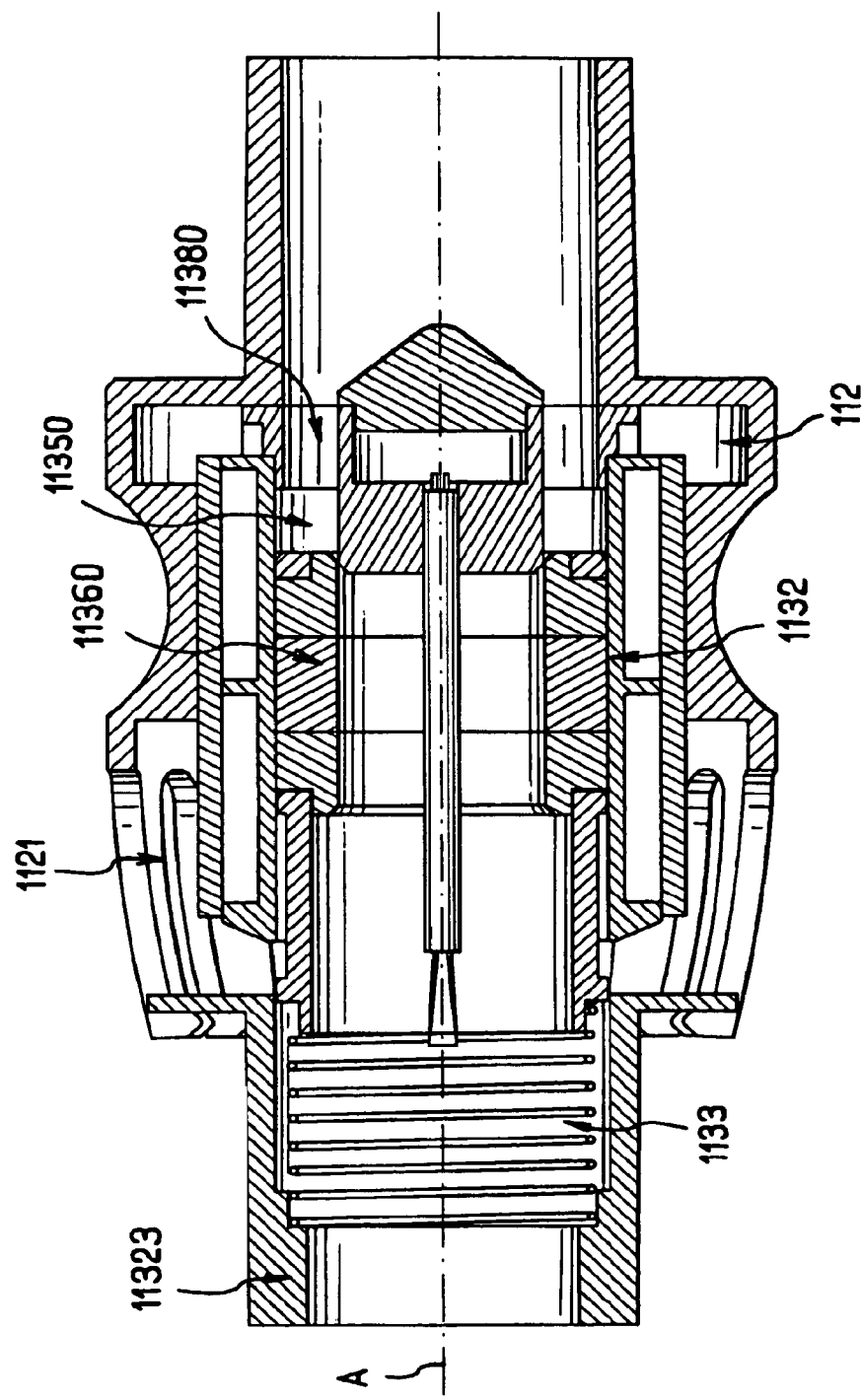
Figure 11E:
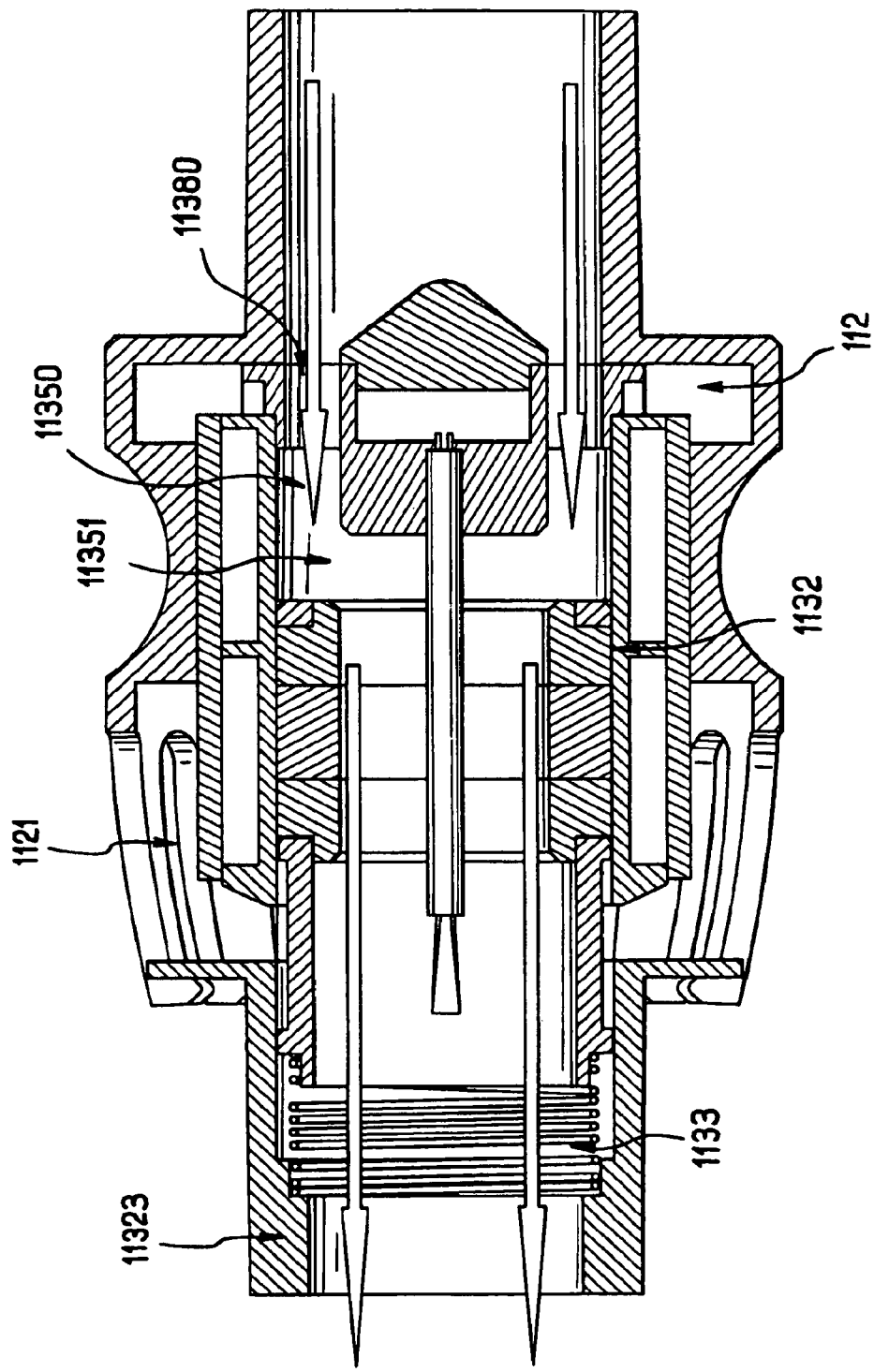

Operation of the valve arrangement of the sixth embodiment described in reference to FIGS. 11*a*-11*f* is more particularly illustrated in reference to FIGS. 11*c*-11*e*.

FIG. 11*c* illustrates the operation of the valve arrangement during expiration of the patient. Such valve arrangement can be controlled with a device (e.g. as illustrated in FIG. 11*f*, or more generally in a schematic manner in FIG. 3, or even more generally in any type of breathing assistance device with control means for controlling the operation of the valve through an adapted electric powering of the coils 11321, 11322).

During such expiration phase, the coils are controlled so as to bring the moving part of the valve arrangement (by attraction of the magnet 11360) in an axial position which closes the holes 11380—thus preventing air to flow through the channels 11350.

In such position of this moving part, the blower cannot send any air to (or receive any air from) the patient.

On the other hand, the proximal end of the valve housing 112 is provided with apertures 1121 which allow the flow expired by the patient to exit to the atmosphere in this position of the moving part.

Indeed, in this position the moving part is blocking the communication between the gas source (blower) and the patient but still allows expiration through the apertures of the valve housing.

In this position the air expired by the patient cannot flow towards the gas source (blower) and thus there is no risk of pollution of the blower elements (or of the duct if there is any between the valve and the gas source).

It is also to be noted that this allows using a blower which is operated in a constant mode (i.e. the rotor of the blower turns at a constant speed). This can be advantageous because it can be desired in some configurations to have a blower operated in such constant mode—which keeps the operation of the blower very simple—while regulating the flow only with the valve (instead of varying the speed of the rotor of the blower).

This also allows avoiding "losing" gas from the blower since no gas can flow through the valve from the blower. And if there is a secondary gas such as oxygen this reveals advantageous since it is economical.

This position of the moving part also corresponds to a reference position of this moving part submitted only to the action of the spring 1133 (i.e. when the coils are not powered).

In FIG. 11*d*, the moving part is controlled (always by the selective electric alimentation of the coils) so as to:
  keep the gas source isolated from the patient (the holes 11380 are liberated but the channel 11350 remains blocked),
  while also blocking the evacuation of air through the apertures 1121.

This is obtained by the controlled position of the moving part (along the longitudinal axis A).

In this mode, the moving part can be translated by selective alimentation of the coils so as to selectively allow a controlled leakage through the apertures 1121 (i.e. by moving the moving part towards the distal end of the valve—towards the right-hand side of FIG. 11—so as to open in a controlled manner the leakage apertures 1121). During such controlled opening of the apertures 1121 the channel 11350 remain blocked and a PEP regulation is provided through the controlled leakage through the apertures 1121.

FIG. 11*e* illustrates a configuration where the position of the moving part is selectively controlled so as to open the channel therefore allowing gas flowing from the blower to the patient through the inner space of the valve. In this configuration the apertures 1121 are also closed.

It is possible to finely control the position of the moving part of such valve arrangement, in, real time, so as to adapt at any time the air communication between the gas source and the patient through the channel 11350, with the opening of the proximal outlet 11351 of the channel 11350.

Operation of the Device when the Gas Source is Disabled

When the gas source S is disabled, e.g. when it breakdowns, the patient P must however be able to breathe. The gas regulating valve according to the invention allows the patient P to breathe normally in such a case.

The controller of the breathing assistance device will namely operate the gas regulating valve so that the leakage orifice remains opened or at least partially opened during both inspiration and expiration phases.

During the expiration phase, the patient P will namely be able to expire through the gas regulating valve as in normal operation of the breathing assistance device.

Indeed, during expiration phases the pressurized gas, coming from the gas source, has only a role for controlling the PEP. However the controller allows a very precise and real time control of the opening of the leakage orifice through the control of the obstruction element. Therefore the absence of pressurized gas coming from the gas source can be counterbalanced in specifically operating the opening of the leakage orifice.

The inspiration phase is also possible as the leakage orifice of the gas regulating valve is opened and allows a gas flow between the inside and the outside of the gas regulating valve. Therefore the patient P will be able to inspire air from the atmosphere through the leakage orifice of the gas regulating valve.

Operation of the Device when the Controller is Disabled

When the controller is disabled, e.g. when the controller breakdowns, the obstruction means cannot be controlled anymore. Therefore a return is provided within the gas regulating valve so that the leakage orifice remains opened in the absence of signal from the controller.

The leakage orifice of the gas regulating valve remaining opened when the controller is disabled, the patient P can both inspire and expire through the leakage orifice of the gas regulating valve.

However, the opening of the leakage orifice being not controllable, it will not be possible to control the PEP anymore.

The gas regulating valve (40;50) of the first and second embodiments comprise a return that consists in the metallic toric sheath (441,541) and the toric magnet (444,544). The toric magnet (444,544) being coaxially disposed within the metallic toric sheath (441,541), this naturally defines a magnetic equator $M_E$.

Indeed, as illustrated in FIG. 7c, the toric magnet 73, in the absence of signal from the controller, remains located in the centre of the metallic toric sheath 74 because of the magnetic forces operating between the toric magnet 73 and the metallic toric sheath 74. The plan defined by the position of the toric magnet 73 is the magnetic equator $M_E$.

The obstruction element 72 of the gas regulating valve is preferably shaped so that the leakage orifice 71 is widely opened when the controller is disabled, that is when the toric magnet 73 of the obstruction element 72 is located on the magnetic equator $M_E$.

The gas regulating valve 60 of the third embodiment of the invention also comprises a return. This return comprises the spring 626 and the screw 627.

As illustrated in FIGS. 6d and 6e, the spring 626 is a compression spring. This compression spring 626 is compressed when the controller controls the coil 621 so that the magnetic element abuts against the circular ridge of the first aperture 614, that is when the leakage orifice is closed (as illustrated in FIG. 6d).

If the controller is disabled, the magnetic element will not be constraint by the coil 621 anymore and is therefore able to translate freely in the toric space 6227. The magnetic element being however coupled with the compression spring 626 via the magnet guide 623, the compression spring 626 draws the magnetic element against the top disc of the armature 622.

In case the controller is disabled, the compression spring 626 will translate the magnetic element of the obstruction element 62, having therefore a leakage orifice widely opened (as illustrated in FIG. 6e).

Finally, as already explained, a return means is also foreseen within the gas regulating valve according to the fourth and fifth embodiments, this return being embodied by the membrane 925.

Indeed, the membrane 925 is made in a material with a high resilience. The specific form of the membrane 925, and in particular the use of a bellows 9255 having a convex curvature oriented towards the walls of the valve. Indeed, if the controller 35 are disabled, the coil 921 is not constraint anymore, but the natural resilience of the material in addition to the specific form of the membrane 925 will cause the pusher element 927 and the coil 921 attached therewith to move back to a position where the leakage orifice 931 are not obstructed anymore. Once again, the patient P will thus be able to breathe freely through the valve.

Further, the pressure within the duct enhances the returns function of the membrane 925 because of its particular design. Indeed, the inner pressure, and more particularly the inspiratory pressure, deforms the membrane 925 in a way that further maintains the coil 921 in its position where the leakage orifice 931 is opened. The bellows 9255 are more precisely deformed in a way that draws the cylindrical portion 9253 and the annular portion 9251, so that the pusher element 927 is further maintained in the open position.

In the case of the valve arrangement of FIG. 11 the moving part comes in the reference position illustrated in FIG. 11c when the coils are not powered.

Operation of the Device when Both the Gas Source and the Controller are Disabled In this case, the patient P will be able to breathe thanks to the return provided in the gas regulating valve. Indeed it has been seen above that the gas source S does not provide a solution for the breathing assistance device to be operated when the controller is disabled.

Therefore, when both the gas source and the controller are disabled, the breathing assistance device according to the invention is operated in the same way as when only the controller is disabled.

The reader will have understood that many modifications may be made without going beyond the new information and the advantages described herein. Consequently, all modifications of this type shall be within the scope of breathing assistance device and methods as defined in the attached claims.

The invention claimed is:

1. A gas regulating valve for use with a breathing assistance device, adapted to be interposed in a gas transmission duct of the breathing assistance device at a location proximal to a patient, and comprising:
    a casing having a proximal portion and a distal portion that are coaxially coupled together and comprise a passage therethrough to allow a supply of pressurized gas to circulate from a gas source to a patient in use;
    a leakage orifice to atmosphere formed in the proximal portion;
    an obstruction element including a movable element coupled to an obstructing piece capable of varying the opening of the leakage orifice; and
    a controller to control the movement of the obstruction element,
    wherein, the movable element surrounds the passage and is constructed to be sealingly separated from the supply of pressurised gas in the passage during use.

2. The valve according to claim 1, wherein the obstructing piece is an elastic membrane.

3. The valve according to claim 2 wherein the elastic membrane is made from rubber or silicone.

4. The valve according to claim 2, wherein the elastic membrane seals the movable element from the passage.

5. The valve according to claim 1 wherein the obstruction element is an electromagnetic obstruction element.

6. The valve according to claim 5, wherein the obstruction element further includes a magnetic element and the movable element is a coil and the coil surrounds the magnetic element.

7. The valve according to claim 6, wherein the obstruction element comprises a metallic armature that is fixed coaxially within the distal portion.

8. The valve according to claim 7 wherein the armature comprises an inner cylindrical portion and an outer cylindrical portion coupled together by an annular portion, the inner cylindrical portion having a diameter smaller than the outer cylindrical portion.

9. The valve according to claim 8, wherein the movable element is located within the outer cylindrical portion of the armature and translatable therein.

10. The valve according to claim 8, wherein a magnetic element is fixed to the inner cylindrical portion of the armature and is configured to control the movement of the moveable element.

11. The valve according to claim 8, wherein the inner cylindrical portion of the armature formed part of the passage for the supply of the pressurized gas.

12. The valve according to claim 8 wherein the proximal end of the outer cylindrical portion includes an annular ridge adapted to couple to the obstruction piece.

13. The valve according to claim 2, wherein the obstructing piece includes a pusher element adapted to deform the membrane to vary the opening of the leakage orifice.

14. The valve according to claim 1 further comprising at least one sensor for sensing flow and/or pressure in the gas passage, the sensor being associated with the controller.

15. The valve according to claim 14, wherein the distal portion includes an external chamber adapted to receive the at least one sensor.

16. The valve according to claim 15, further comprising a processing module configured to connect the sensor to the controller.

17. The valve according to claim 16, wherein the processing module is removably connected to the casing.

18. The valve according to claim 17, wherein the processing module includes a clip for removably coupling the processing module to the casing.

19. The valve according to claim 1 further comprising a breathing assistance device for a patient breathing is successive cycles, each cycle being defined by at least an inspiration phase and at least an expiration phase, said breathing assistance device comprising:
 a gas source of respiratory pressurized gas;
 a patient interface device;
 a gas transmission duct comprising a distal end coupled to said gas source and a proximal end adapted to couple to the patient interface device;
 a controller to control the operation of the device;
 wherein the gas regulating valve is interposed in the gas transmission duct near the proximal end of the gas transmission duct.

20. A gas regulating valve for use with a breathing assistance device, adapted to be interposed in a gas transmission duct of the breathing assistance device at a location proximal to a patient, and comprising:
 a casing including a gas flow duct and a housing;
 a leakage orifice to atmosphere formed in the housing;
 an obstruction element within the housing;
 a protection element within the housing between the leakage orifice and the obstruction element and
 the obstruction element being adapted to move in response to control by a controller,
 wherein the gas flow duct includes a proximal end adapted to couple to the transmission duct in the direction of a patient and a distal end adapted to couple to the transmission duct in the direction of a gas source, the gas flow duct configured to receive a flow of breathable gas between the gas source and the patient;
 wherein a first side of the housing is in communication with the gas flow duct; and
 wherein, the obstruction element includes a movable element, the movable element acting on the protection element to vary the opening of the leakage orifice in response to a signal from the controller, the protection element isolating the obstruction element from the gas flow duct.

21. The valve according to claim 20, wherein the protection element is a membrane.

22. The valve according to claim 21, wherein the membrane is made from rubber or silicone.

23. The valve according to claim 22, wherein the housing is mounted transversally relative to the gas transmission duct.

24. The valve according to claim 21, wherein the obstruction element is an electromagnetic obstruction element.

25. The valve according to claim 24, wherein obstruction element further comprises a coil that surrounds the movable element and the movable element includes a magnetic element.

26. The valve according to claim 25, wherein the obstruction element comprises a metallic armature that is fixed within the housing.

27. The valve according to claim 26 wherein the armature comprises a top disc having a top circular opening; a bottom disc having a larger bottom circular opening, the top disc and bottom disc being coaxially coupled together by a peripheral coaxial cylindrical portion having the same diameter as the bottom circular opening; an inner cylindrical passage extending into the bottom circular opening; and a toric space between the inner cylindrical passage and peripheral coaxial cylindrical portion.

28. The valve according to claim 27, wherein the movable element is located within toric space of the armature and translatable therein.

29. The valve according to claim 27, wherein the coil is fixed in a position surrounding the armature to control the movement of the magnetic element.

30. The valve according to claim 27, wherein a peripheral edge of the protection element is coupled to the armature.

31. The valve according to claim 20, wherein the obstruction element further comprises a return means to ensure the leakage orifice is opened in the absence of the signal from the controller.

32. The valve according to claim 31, wherein the return means is a compression spring.

33. The valve according to claim 20 further comprising at least one sensor for sensing flow and/or pressure in the gas passage, the sensor being located in the housing and associated with the controller.

34. The valve according to claim 33, further comprising a processing module configured to connect the sensor to the controller.

35. The valve according to claim 20, further comprising a housing cover coupled to a second side of the housing.

36. The valve according to claim 20 further comprising a breathing assistance device for a patient breathing is successive cycles, each cycle being defined by at least an inspiration phase and at least an expiration phase, said breathing assistance device comprising:
- a gas source of respiratory pressurized gas;
- a patient interface device;
- a gas transmission duct comprising a distal end coupled to said gas source and a proximal end adapted to couple to the patient interface device;
- a controller to control the operation of the device;
- and wherein the gas regulating valve is interposed in the gas transmission duct near the proximal end of the gas transmission duct.

* * * * *